US008597925B2

(12) United States Patent
Hwang et al.

(10) Patent No.: US 8,597,925 B2
(45) Date of Patent: Dec. 3, 2013

(54) HOMOGENEOUSLY-STRUCTURED NANO-CATALYST/ENZYME COMPOSITE ELECTRODE, FABRICATING METHOD AND APPLICATION OF THE SAME

(75) Inventors: Bing-Joe Hwang, Taipei (TW); Min-Hsin Yeh, Taipei (TW); Shih-Hong Chang, Taipei (TW); Chung-Chiun Liu, Cleveland Hts, OH (US); Chao-Shan Chou, Tainan (TW)

(73) Assignee: National Taiwan University of Science and Technology, Taipei (TW)

( * ) Notice: Subject to any disclaimer, the term of this patent is extended or adjusted under 35 U.S.C. 154(b) by 394 days.

(21) Appl. No.: 12/887,768

(22) Filed: Sep. 22, 2010

(65) Prior Publication Data

US 2011/0155576 A1 Jun. 30, 2011

(30) Foreign Application Priority Data

Dec. 30, 2009 (TW) ............................... 98145948 A

(51) Int. Cl.
*C12N 9/00* (2006.01)
*C07K 14/00* (2006.01)

(52) U.S. Cl.
USPC .......................................... 435/183; 530/300

(58) Field of Classification Search
None
See application file for complete search history.

(56) References Cited

U.S. PATENT DOCUMENTS

| 5,227,042 A * | 7/1993 | Zawodzinski et al. ..... 204/403.1 |
| 6,042,714 A | 3/2000 | Lin et al. |
| 2005/0150762 A1 * | 7/2005 | Butters et al. ............ 204/403.01 |

FOREIGN PATENT DOCUMENTS

| CN | 1057672 A | 1/1992 |
| CN | 1871378 A | 11/2006 |
| TW | 344029 | 11/1998 |
| TW | 200528710 | 9/2005 |
| TW | 200718939 | 5/2007 |

OTHER PUBLICATIONS

Wu et al., "Amperometric glucose biosensor based on multilayer films via layer-by-layer self-assembly of multi-wall carbon nanotubes, gold nanoparticles and glucose oxidase on the Pt electrode", Biosensors and Bioelectronics 22: 2854-2860 (2007).*
Yu-Chen Tsai et al., "Cast Thin Film Biosensor Design Based on a Nafion Backbone, a Multiwalled Carbon Nanotube Conduit, and a Glucose Oxidase Function", *Langmuir* 2005, 21, 3653-3658.
Adriana Mignani et al., "Electrodeposited glucose oxidase/anionic clay for glucose biosensors design", Analytica Chimica Acta 577 (2006) 98-106.
Qing Kang et al., "An electro-catalytic biosensor fabricated with Pt-Au nanoparticle-decorated titania nanotube array", Bioelectrochemistry 74 (2008) 62-65.
Jue Lu et al., "Simple Fabrication of a Highly Sensitive Glucose Biosensor Using Enzymes Immobilized in Exfoliated Graphite Nanoplatelets Nafion Membrane", Chem. Mater. 2007, 19, 6240-6246.
San Hua Lim et al.,"A glucose biosensor based on electrodeposition of palladium nanoparticles and glucose oxidase onto Nafion-solubilized carbon nanotube electrode", Biosensors and Bioelectronics 20 (2005) 2341-2346.
Jian-Ding Qiu et al., "Electrochemically deposited nanocomposite film of CS-Fc/Au NPs/GOx for glucose biosensor application", Biosensors and Bioelectronics 24 (2009) 2920-2925.
Xiandong Zeng et al., "Electrodeposition of chitosan-ionic liquid-glucose oxidase biocomposite onto nano-gold electrode for amperometric glucose sensing", Biosensors and Bioelectronics 24 (2009) 2898-2903.
Xu Chen et al., "Organically Modified Sol-Gel/Chitosan Composite Based Glucose Biosensor", Electroanalysis 2003, 15, No. 7, 608-612.
Henning Sakslund et al., "Development and evaluation of glucose microsensors based on electrochemical codeposition of ruthenium and glucose oxidase onto carbon fiber microelectrodes", Journal of Electroanalytical Chemistry 397 (1995) 149-155.

* cited by examiner

*Primary Examiner* — Anand Desai
(74) *Attorney, Agent, or Firm* — Rabin & Berdo, P.C.

(57) ABSTRACT

A homogeneously-structured catalyst/enzyme composite structure formed by electrophoresis deposition (EPD) method. Catalyst and enzyme are simultaneously deposited onto the electrode surface by the EPD method, so as to form a film of catalyst/enzyme composite thereon. The film of catalyst/enzyme composite includes enzyme for catalyzing the biochemical reaction, and catalyst for increasing the rate of the electrochemical reaction, which are homogeneously mixed and forms a stable and three-dimensional structure. Also, this homogeneously-structured catalyst/enzyme composite is applicable as a working electrode of the bioreceptor in a mini-biosensor.

9 Claims, 15 Drawing Sheets

HOMOGENEOUSLY-STRUCTURED NANO-CATALYST/ENZYME COMPOSITE ELECTRODE, FABRICATING METHOD AND APPLICATION OF THE SAME

This application claims the benefit of Taiwan application Serial No. 98145948, filed Dec. 30, 2009, the subject matter of which is incorporated herein by reference.

BACKGROUND OF THE DISCLOSURE

1. Field of the Disclosure

The disclosure relates in general to a catalyst/enzyme structure and a fabricating method thereof, and more particularly to a homogeneously-structured catalyst/enzyme composite structure, a fabricating method and an application of the same. The method could be applied in a wide application such as an organic molecule sensor or a bioreceptor, such as an immobilization for a substrate of the mini sensor, etc.

2. Description of the Related Art

FIG. 1 illustrates a schematic diagram of a basic structure of one kind of a biosensor. The basic structure of the biosensor comprises a biological recognition element (bioreceptor) 11, a signal transducer 12 and a signal processor 13. During a theoretical sensing process of the biosensor, the variance quantity of the physical or chemical variance of the biological recognition element 11, having biochemical specificity, resulted from the binding or reacting with a test compound 15 would transform into a significant electronic signal through the signal transducer 12. The signal could be amplified and recorded by the signal processor 13 for convenience of subsequent qualitative and quantitative analysis.

Biological materials used as sensing elements for the biosensor usually comprise the following kinds: (a) enzyme, (b) antibody and antigen, (c) nucleic acid, (d) receptor, and (e) cell organelle. The biosensors fabricated by using different biological sensing materials have specific advantages and disadvantages. Among the many kinds of the biological sensing materials, enzymes are the most-early and most-frequently used. Generally speaking, the enzyme has characteristics of specificity (i.e. one kind of the enzyme can only catalyze one specific matrix), repeatability, heat susceptivity, acid-base susceptivity, etc. The catalytic behavior of binding with a test compound of an enzyme can be applied in a biosensor.

As universal economic development is improved, life and diet of human being are changed substantially. Globally, the main causes of death have been shifted from acute infections to chronic diseases. Among many chronic diseases, diabetes mellitus (often simply referred to as diabetes) is by far the most common chronic disease affecting great population. Statistically, diabetes takes the fourth place of ten major causes of death, published by National Health Administration of Taiwan in 2007. Although medical technology has made progress, diabetes usually cannot be cured completely. Diabetes without proper treatments and being controlled can cause many complications. This contributes significant burdens on individuals, families, societies and countries. For example, it not only consumes societal medical resources but also affect qualities of lives on a patient and families of that. A biosensor having an excellent performance can be used for properly monitoring and tracking a blood glucose concentration of a person for preventing and easing a complication. An intention of an early discovery and an early remedy can be also achieved. A mini sensor is a portable apparatus, which is easy to carry and measures a concentration of a test compound instantly.

There are a variety of technical combinations or methods could be adopted to make a completed biosensor for monitoring diabetes. In other words, a sensing device for analyzing glucose can be assembled by using many kinds of biochemical elements collocated with proper signal transducers. In many researches, an electrochemical glucose biosensor having glucose oxidases fixed therein is used for investigating analysis of the glucose. Therefore, glucose oxidases (GOD) are the most-frequently-used enzymes for these researches.

A glucose oxidase is one kind of compound comprising two similar glycoproteins of quadratic elements. The glycoproteins of quadratic elements are connected by a disulfide group. Each subunit comprises a complementation group of flavin adenine dinucleotide (FAD) having a following molecular structure:

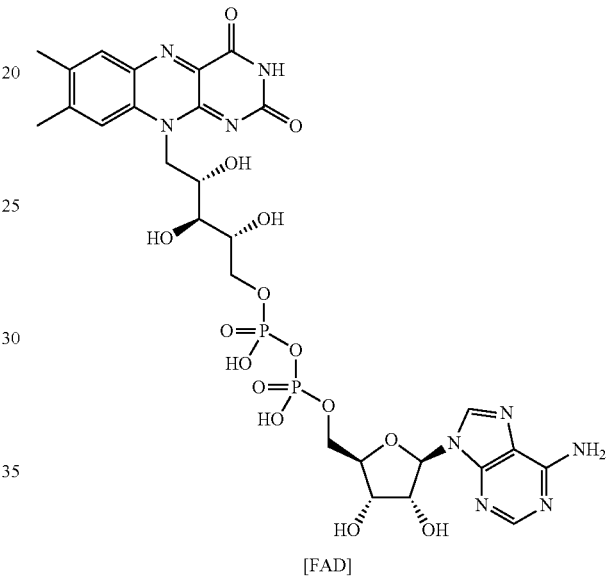

[FAD]

In an existence of an electron substrate, the GOD could catalyze a β-D-glucose to become a D-glucono-δ-lactone. In addition, the FAD on the GOD would be reduced to form a $FADH_2$, as shown as an equation (1-1):

The D-glucono-δ-lactone would further react with the water in the solution to form a gluconic acid, as shown as a equation (1-2):

The equation (1-1) and the equation (1-2) would be combined to obtain an equation (1-3):

The oxygen in the solution could be an electron acceptor of the $GOD(FADH_2)$. Therefore, the electron of the GOD ($FADH_2$) would transfer to the oxygen and reduce the oxygen to become a hydrogen preoxide. In addition, the GOD ($FADH_2$) is oxidized to become a GOD(FAD) shown as a equation (1-4):

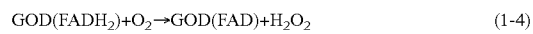

The equation (1-4) and the equation (1-3) could be combined to obtain a equation (1-5):

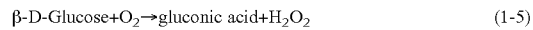

The biosensor as shown in FIG. 1 has advantages of easily performing an analysis treatment and an output display by transforming a biochemical signal into an electronic signal. The biosensor can be assembled as different types as being applied for different electronic devices. In FIG. 1, the signal transducer 12 can transform the physical or chemical variance quantity into an electronic signal that could be measured. In addition, in a proper condition, the strength of the electronic signal is also was proportioned to a concentration of a specific compound. Three types of the signal transducers 12 of different structures and energy conversion mechanisms are: (1) electrochemical biosensor, (2) optical biosensor, and (3) mass biosensor. The signal transducers 12 of different types have respective advantages and disadvantages.

The electrochemical biosensor uses an electrochemical measuring method using a potential, an electric current or a signal transducer, and a bioreceptor having a modified electrode used for carrying out a catalysis reaction of a test compound in a test sample with a fixed biological molecule for generating a product. As the product reacts with a catalyst on the surface of the electrode by an electrochemical oxidation-reduction reaction, the concentration of the test compound can be obtained by an indirect determination method using an output electric current or voltage, or a variance quantity of electric conductivity due to the reaction. During a process of sensing glucose of a conventional glucose receptor, for example, a glucose oxidase fixed on a surface of an electrode would react with a glucose in a test solution by a catalysis reaction to form hydrogen peroxide. Hydrogen peroxide would diffuse onto the surface of the electrode to react with the catalyst material by an electrochemical oxidation-reduction reaction to generate an electric current signal. Therefore, the electrochemical bioreceptor has the bioreceptor layer having specificity for the test compound. Moreover, the electrochemical bioreceptor also has the advantage of an electrochemical transducer. Expensive and complicated instruments are not necessary. The signal response time is very short. The linear detecting range is extensive. In addition, the operating process is simple and easy. Therefore, the convenience of the electrochemical biosensor is very helpful for future popularization for clinical application. Three types of the electrochemical transducers according to properties of electronic signals of which are a potentiometric type, an amperometric type, and a conductometric type. The amperometric type electrochemical transducer is used most frequently.

In a conventional method for fabricating a mini sensor, a catalyst is fixed on a working electrode of the mini sensor by a screen printing method. After the mini sensor is fabricated, an enzyme is fixed on the surface of which by an enzyme immobilization method. FIG. 2 illustrates a schematic diagram of a layer-shape structure of a conventional mini sensor. The disadvantage of the mini sensor fabricated by the conventional method comes from a structure of a layered stack of the catalyst/enzyme on the surface of the working electrode comprising a substrate 21 and a silver wire 22. The inner layer and the outer layer of the layered stack of the catalyst/enzyme are a catalyst layer 24 and an enzyme layer 26, respectively. For example, the enzyme layer 26 of the glucose oxidase, formed by the conventional immobilization method, on the surface of the electrode has a thickness of about 60 µm-80 µm. The enzyme layer 26 of a thickness of the layered structure as shown in FIG. 2 would be an obstructer obstructing the diffusion of hydrogen peroxide into the catalyst layer 24. In addition, the obstructer layer would result in a mass transfer resistance for the diffusion of hydrogen peroxide generated through the glucose oxidase on the surface into the surface of the electrode. Therefore, the sensing ability of the mini sensor is reduced. Especially, the sensitivity of the receptor for the glucose of high concentration is reduced.

Moreover, the conventional method for fabricating the mini sensor needs complicated steps. In addition, the catalyst and the enzyme are the expensive materials. However, the conventional method for fabricating the mini sensor having a desired sensing ability often requires excess of the catalyst and the enzyme to make. Therefore, the production cost of the mini sensor is very high.

SUMMARY OF THE DISCLOSURE

The disclosure is directed to a homogeneously-structured catalyst/enzyme composite and a fabricating method thereof, that having high reproducibility, repeatability and accuracy. In addition, the homogeneously-structured catalyst/enzyme composite and the fabricating method thereof could be applied in a wide application such as an organic molecule sensor or a bioreceptor, such as an immobilization for a substrate of the mini sensor, etc.

According to the present disclosure, a catalyst-enzyme composite film structure is provided. The catalyst-enzyme composite film structure comprises a plurality of homogeneously mixed and distributed enzymes for catalyzing a biochemical reaction and catalyst particles for increasing a rate of an electrochemical reaction. In one embodiment, the catalyst/enzyme composite film is formed on a surface of a substrate by forming the plurality of the catalysts and the enzymes simultaneously by an electrophoresis deposition method (EPD). The catalyst/enzyme composite film can be used for a working electrode in a biological recognition element (or bioreceptor) of a mini sensor. A fabricating method for an electrode of a mini sensor is provided. An electrophoresis solution comprising a plurality of catalyst particles and enzymes is provided. A catalyst/enzyme composite film is formed on a surface of a substrate by depositing the catalyst particles and the enzymes simultaneously by an electrophoresis deposition (EPD) method in a proper electrophoresis deposition (EPD) condition. The catalyst/enzyme composite film comprises the homogeneously mixed catalyst particles and enzymes.

According to the present disclosure, a mini sensor is provided. The mini sensor comprises a biological recognition element (or bioreceptor), a signal transducer and a signal processor. After the bioreceptor binds or reacts with a test compound, a change value of a physical/chemical property is generated. The bioreceptor comprises a working electrode comprises a substrate and a catalyst-enzyme composite film formed on a surface of the substrate. The catalyst-enzyme composite film comprises a plurality of homogeneously mixed and distributed catalyst particles and enzymes. The catalyst particles are used for increasing a rate of an electrochemical reaction. The enzymes are used for catalyzing a biochemical reaction. The enzymes and the catalyst particles are deposited on the substrate simultaneously by an electrophoresis deposition (EPD) method to forming a working electrode of a homogeneously-structured catalyst/enzyme composite. The signal transducer transforms a physical/chemical change value of a physical/chemical property into an electronic signal. The signal processor receives and processes the electronic signal generated by the signal transducer. From the experiments, it is verified that the mini sensor can be preserved over 30 days at the room temperature. Therefore, the catalyst/enzyme composite electrode of the present disclosure can be used for fabricating a mini sensor having a homogeneously-structured composite catalyst/enzyme structure having a reproducibility, repeatability and accuracy.

The above and other aspects of the disclosure will become better understood with regard to the following detailed description but non-limiting embodiment(s). The following description is made with reference to the accompanying drawings.

BRIEF DESCRIPTION OF THE DRAWINGS

FIG. 10B represents the ratio of the measured electric current for the solution to the 5 mM glucose solution.

DETAILED DESCRIPTION OF THE DISCLOSURE

Figure 1:
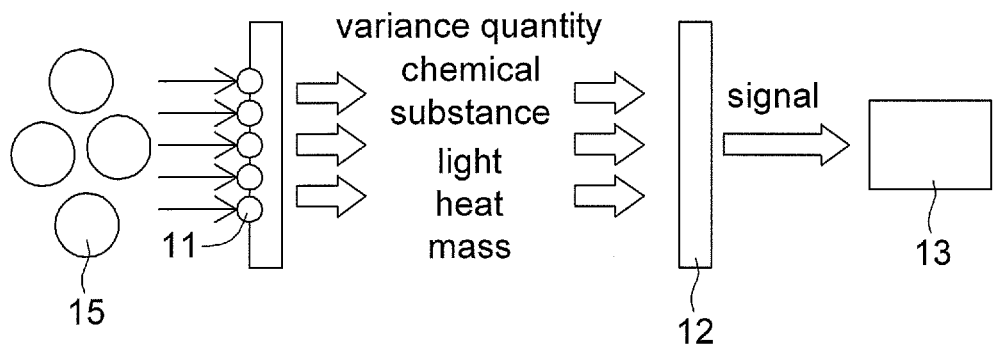
FIG. 1 illustrates a schematic diagram of a basic structure of one kind of a conventional biosensor.
Figure 2:
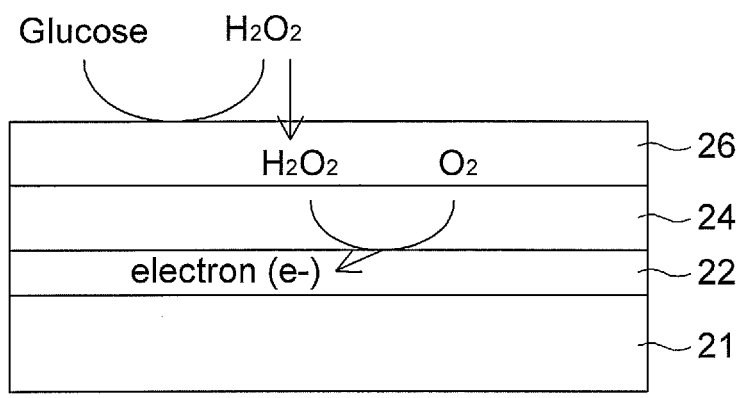
FIG. 2 illustrates a schematic diagram of a layer-shape structure of a conventional mini sensor.
Figure 3:
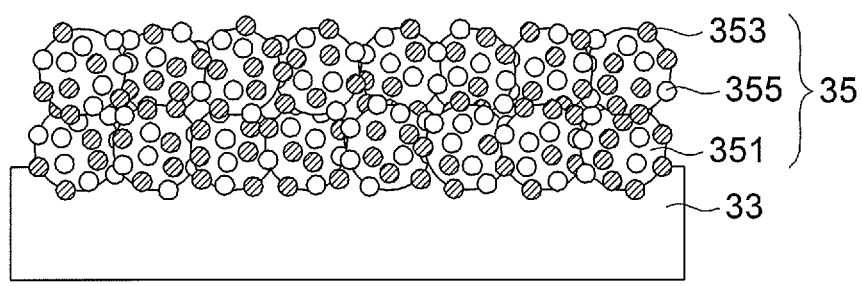
FIG. 3 illustrates a schematic diagram of the catalyst-enzyme composite film structure of one embodiment of the disclosure.

The present disclosure provides a catalyst-enzyme composite film structure having a homogeneous structure, and a fabricating method and an application of the catalyst-enzyme composite film structure. FIG. 3 illustrates a schematic diagram of the catalyst-enzyme composite film structure of one embodiment of the disclosure. A catalyst-enzyme composite film 35 is formed on a surface of a substrate such as a working electrode 33. The catalyst-enzyme composite film 35 comprises a plurality of catalyst particles 353 and a plurality of enzymes 355 that are homogeneously mixed and distributed. The catalyst particles 353 and the enzymes 355 are formed on catalyst supports 351. The enzymes 355 are used for catalyzing a biochemical reaction. The catalyst particles 353 are used for increasing a rate of an electrochemical reaction. In one exemplary embodiment, for example, the enzymes for catalyzing the biochemical reaction react with a biomolecule to form hydrogen peroxide ($H_2O_2$). The catalyst particles for increasing the rate of the electrochemical reaction carry out an electrochemical oxidation-reduction reaction with hydrogen peroxide. Furthermore, in one embodiment, the catalyst support 351 may be a carbon black support (Carbon, XC-72R, available from Cabot Corporstion) for example. An average diameter of the catalyst particles may be between about 0.5 nm and about 100 μm. In embodiments of the present disclosure, the catalyst particles 353 and the enzymes 355 are simultaneously deposited onto the surface of the substrate 33 by an electrophoresis deposition (EPD) method. As applied in a mini sensor, the catalyst particles 353 and the enzymes 355 may be simultaneously deposited onto a surface of a working electrode by the electrophoresis deposition (EPD) method. A depth profile result of an electron spectroscopy for chemical analysis (ESCA) of the catalyst-enzyme composite film formed by simultaneously depositing the catalysts and the enzymes by the electrophoresis deposition (EPD) method verifies that the catalyst-enzyme composite film has a homogeneously-structured layer as shown in FIG. 3.

In embodiments, examples of the enzymes 355 includes an glucose oxidase (EC 1.1.3.4), a malate oxidase (EC 1.1.3.3), a hexose oxidase (EC 1.1.3.5, a cholesterol oxidase (EC 1.1.3.6, an aryl-alcohol oxidase (EC 1.1.3.7), a L-gulonolactone oxidase (EC 1.1.3.8), a galactose oxidase (EC 1.1.3.9), a pyranose oxidase (EC 1.1.3.10), a L-sorbose oxidase (EC 1.1.3.11), a pyridoxine 4-oxidase (EC 1.1.3.12), an alcohol oxidase (1.1.3.13), a (S)-2-hydroxy-acid oxidase (1.1.3.15), an ecdysone oxidase (EC 1.1.3.16), a choline oxidase (EC 1.1.3.17), a secondary-alcohol oxidase (EC 1.1.3.18), a 4-hydroxymandelate oxidase (EC 1.1.3.19), a long-chain-alcohol oxidase (EC 1.1.3.20), a glycerol-3-phosphate oxidase (EC 1.1.3.21), a thiamine oxidase (EC 1.1.3.23), a hydroxyphytanate oxidase (EC 1.1.3.27), an N-acylhexosamine oxidase (EC 1.1.3.29), a polyvinyl-alcohol oxidase (EC 1.1.3.30), a D-Arabinono-1,4-lactone oxidase (EC 1.1.3.37), a vanillyl-alcohol oxidase (EC 1.1.3.38), a nucleoside oxidase ($H_2O_2$-forming) (EC 1.1.3.39), a D-mannitol oxidase (EC 1.1.3.40), a xylitol oxidase (EC 1.1.3.41), a cellobiose dehydrogenase (acceptor) (EC 1.1.99.18), a formate dehydrogenase (EC 1.2.1.2), an aldehyde oxidase (EC 1.2.3.1), a pyruvate oxidase (EC 1.2.3.3), an oxalate oxidase (EC 1.2.3.4), a glyoxylate oxidase (EC 1.2.3.5), a pyruvate oxidase (CoA-acetylating) (EC 1.2.3.6), an aryl-aldehyde oxidase (EC 1.2.3.9), a retinal oxidase (EC 1.2.3.11), an abscisic-aldehyde oxidase (EC 1.2.3.14), an oxoglutarate dehydrogenase (succinyl-transferring) (EC 1.2.4.2), a dihydroorotate oxidase (EC 1.3.3.1), a coproporphyrinogen oxidase (EC 1.3.3.3), an acyl-CoA oxidase (EC 1.3.3.6), a dihydrouracil oxidase (EC 1.3.3.7), a tetrahydroberberine oxidase (EC 1.3.3.8), a tryptophan alpha,beta-oxidase (EC 1.3.3.10), a pyrroloquinoline-quinone synthase (EC 1.3.3.11), a L-galactonolactone oxidase (EC 1.3.3.12), an acyl-CoA dehydrogenase (EC 1.3.99.3), a dihydroorotate dehydrogenase (EC 1.3.99.11), a D-aspartate oxidase (EC 1.4.3.1), a L-amino-acid oxidase (EC 1.4.3.2), a D-amino-acid oxidase (EC 1.4.3.3), an amine oxidase (flavin-containing) (EC 1.4.3.4), a pyridoxal 5'-phosphate synthase (EC 1.4.3.5), an amine oxidase (copper-containing) (EC 1.4.3.6), a D-glutamate oxidase (EC 1.4.3.7), a ethanolamine oxidase (EC 1.4.3.8), a putrescine oxidase (EC 1.4.3.10), a L-glutamate oxidase (EC 1.4.3.11), a cyclohexylamine oxidase (EC 1.4.3.12), a protein-lysine 6-oxidase (EC 1.4.3.13), a L-lysine oxidase (EC 1.4.3.14), a D-glutamate(D-aspartate) oxidase (EC 1.4.3.15), a L-aspartate oxidase (EC 1.4.3.16), a glycine oxidase (EC 1.4.3.19), a L-lysine 6-oxidase (EC 1.4.3.20), an amine dehydrogenase (EC 1.4.99.3), a FMN reductase (EC 1.5.1.29), a sarcosine oxidase (EC 1.5.3.1), an N-methyl-L-amino-acid oxidase (EC 1.5.3.2), an N6-methyl-lysine oxidase (EC 1.5.3.4), a (S)-6-hydroxynicotine oxidase (EC 1.5.3.5), a (R)-6-hydroxynicotine oxidase (EC 1.5.3.6), a L-pipecolate oxidase (EC 1.5.3.7), a dimethylglycine oxidase (EC 1.5.3.10), a polyamine oxidase (EC 1.5.3.11), a dihydrobenzophenanthridine oxidase (EC 1.5.3.12), a trimethylamine dehydrogenase (EC 1.5.8.2), a L-pipecolate dehydrogenase (EC 1.5.99.3), a cytokinin dehydrogenase (EC 1.5.99.12), an NAD(P)H oxidase (EC 1.6.3.1), an NAD(P)H dehydrogenase (quinone) (EC 1.6.5.2), an nitrite reductase (NO-forming) (EC 1.7.2.1), an nitroalkane oxidase (EC 1.7.3.1), an urate oxidase (EC 1.7.3.3), a 3-aci-nitropropanoate oxidase (EC 1.7.3.5), a dihydrolipoyl dehydrogenase (EC 1.8.1.4), a sulfite oxidase (EC 1.8.3.1), a thiol oxidase (EC 1.8.3.2), a glutathione oxidase (EC 1.8.3.3), a methanethiol oxidase (EC 1.8.3.4), a prenylcysteine oxidase (EC 1.8.3.5), a 3-hydroxyanthranilate oxidase (EC 1.10.3.5), a rifamycin-B oxidase (EC 1.10.3.6), an NADH peroxidase (EC 1.11.1.1), a 2-nitropropane dioxygenase (EC 1.13.11.32), a lysine 2-monooxygenase (EC 1.13.12.2), a lactate 2-monooxygenase (EC 1.13.12.4), a photinus-luciferin 4-monooxygenase (ATP-hydrolysing) (EC 1.13.12.7), a phenylalanine 2-monooxygenase (EC 1.13.12.9), a clavaminate synthase (EC 1.14.11.21), an naphthalene 1,2-dioxygenase (EC 1.14.12.12), a 4-aminobenzoate 1-monooxygenase (EC 1.14.13.27), an alkanal monooxygenase (FMN-linked) (EC 1.14.14.3), a phenylalanine 4-monooxygenase (1.14.16.1), an anthranilate 3-monooxygenase (EC 1.14.16.3), a monophenol monooxygenase (EC 1.14.18.1), a lathosterol oxidase (EC 1.14.21.6), a superoxide dismutase (EC 1.15.1.1), a superoxide reductase (EC 1.15.1.2), a xanthine dehydrogenase (EC 1.17.1.4), a xanthine oxidase (EC 1.17.3.2), a 6-hydroxynicotinate dehydrogenase (EC 1.17.3.3), a reticuline oxidase (EC 1.21.3.3), and a ribulose-bisphosphate carboxylase (EC 4.1.1.39).

In one embodiment, the catalyst particles 353 may be a unary metal (M), a binary metal (M-X), a unary metal oxide (MOy), a binary metal oxide (MOy-XOy), a metal-metal oxide composite material (M-MOy) or a combination of which. y is smaller than 3. M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Ir, Tm, Lu, Ta, W, Os, Ir, Pt, Au, Pb, and Bi. In one embodiment, for example, the catalyst particles 353 may be composed of the binary metal and the binary metal oxide. A molar ratio of the metal of the catalyst particles 353 is bigger than 0 and smaller than 100%.

The following describes one embodiment of a glucose receptor having a working electrode and an electrochemical transducer in which nano PtIr catalyst particles are used as the catalyst particles, and glucose oxidases are used as the enzymes. In addition, the nano PtIr catalyst particles and the glucose oxidases are simultaneously deposited on the working electrode. In this exemplary embodiment, the glucose oxidases, which are the enzymes for catalyzing the biochemical reaction, react with a biomolecule to form hydrogen peroxide ($H_2O_2$). The nano PtIr catalyst particles, which are the catalyst particles, carry out an electrochemical oxidation-reduction reaction with hydrogen peroxide. In the embodiment, the catalyst and the enzyme are simultaneously deposited on the surface of the working electrode of a mini sensor for easily forming a mini sensor having a stable homogeneous catalyst-enzyme composite structure. As presented below, two parts of (C1) an analysis for the electrode structure, having the nano PtIr catalyst particles and the glucose oxidases simultaneously deposited thereon by the electrophoresis deposition (EPD) method, of the mini sensor; and (C2) an analysis for an electrochemical characteristic of the mini sensor having the nano PtIr catalyst particles and the glucose oxidases simultaneously deposited, are described in details for illustration.

It is understood that the present disclosure is not limited to any one of the following embodiments that relate to the nano PtIr (binary metal) catalyst and the glucose oxidases. Moreover, other kinds of the catalysts and the enzymes described may be properly used according to the practical condition for forming the homogeneous catalyst-enzyme composite structure by the electrophoresis deposition (EPD) method. Therefore, the present disclosure is also not limited to the glucose receptor.

C: Depositing Nano PtIr Catalyst Particles and Glucose Oxidases to Mini Sensor by Electrophoresis Deposition (EPD) Method According to the present disclosure, the catalyst particles and the enzymes are simultaneously deposited to the mini sensor by the electrophoresis deposition (EPD) method depositing. The electrophoresis deposition (EPD) method uses a driving force generated by an electric field to deposit charged particles in a suspension liquid onto the working electrode. According to the embodiment of the present disclosure, the electrophoresis deposition (EPD) method simultaneously deposits the nano PtIr catalyst particles and the glucose oxidases onto the mini sensor. In one embodiment, an electrophoresis solution of a stationary phase suspension is obtained by homogeneously mixing a proper amount of the nano PtIr catalyst particles, glucose oxidases and Nafion in phosphate buffered saline (PBS) solution. The electrophoresis solution has the charged molecules of the Nafion exhibiting a negative electricity due to a sulfite functional group generated from a hydrogen ion dissociation in water and the glucose oxidases (the PH value of which is 4.2) exhibiting a negative electricity in the phosphate buffered saline (PBS) (the PH value of which is about 7.4). Since the Nafion ionomer would react with and thus adhere to a support of the nano PtIr catalyst particles, a surface of the support would have negative electricity. Therefore, under the driving force of the electric field, the Nafion ionomer, the glucose oxidases and the nano PtIr catalyst particles that all have negative electricity would move to a anode having a positive charge. Thus, the Nafion ionomer, the glucose oxidases and the nano PtIr catalyst particles are deposited on the surface of the working electrode of the mini sensor at the same time.

Parameters the electrophoresis deposition (EPD) method generally relate to (1) the electrophoresis solution condition and (2) the electrophoresis process condition. The electrophoresis solution condition relates to a size and a zeta potential of the suspension particle, and a permittivity, an electric conductivity, a viscosity and a stability of the solution, etc. The electrophoresis process condition relates to a depositing time, a potential, a concentration of the suspension particles in the solution, an electric conductivity of the substrate, etc.

In one embodiment, the electrophoresis solution is obtained with the following steps. A proper amount of the nano metal catalyst and 5% Nafion in a solvent are well mixed in a supersonic vibrating apparatus for 30 minutes. Next, a proper amount of the glucose oxidases is added and well mixed in the electrophoresis solution (note the supersonic vibrating apparatus should not be used in this step for avoiding causing effect on the activity of enzyme. Next, the electrophoresis solution is preserved at 4° C. The electrophoresis deposition (EPD) has the following steps. The electrophoresis solution is placed on a stirring apparatus for well mixing the particles in the solution. Next, the to-be-deposited mini sensor is electrically connected with a slot socket connecting to a constant potential instrument. The electrophoresis deposition (EPD) process is performed by applying a constant electric potential or a constant electric current. After the deposition step, the mini sensor having the catalyst and the enzyme deposited thereon is dried in a nature air. Next, the mini sensor ready for use is preserved in a clip chain bag (zip bag). Note the present disclosure is not limited to the steps and parameters described in the embodiments. Therefore, the steps and parameters can be varied according to the actual application of the present disclosure.

C1: Structure Analysis for Electrode with Nano PtIr Catalyst Particles and Glucose Oxidases Simultaneously Deposited Thereon by Electrophoresis Deposition (EPD) Method in Mini Sensor In embodiments, a structure analysis is carried out for the electrode of the mini sensor that has the nano PtIr catalyst particles and the glucose oxidases simultaneously deposited thereon by the electrophoresis deposition (EPD) method. In which, an element depth-profile analyses by an electron spectroscopy for chemical analysis (ESCA) is used to investigate distributions of different charged particles deposited on the surface of the electrode by the electrophoresis deposition (EPD) method. The result as shown in FIG. 3 confirms that the homogeneously-structured catalyst/enzyme composite film is formed on the surface of the substrate.

The element depth-profile analyses by the electron spectroscopy for chemical analysis (ESCA) adopted in embodiments for observing the distributions of the different charged particles deposited by the electrophoresis deposition (EPD) method on the surface of the substrate is described as the following.

From element analyses results, obtained according to binding energies of Pt, Ir, N and F and XPS depth profiles, formed by etching by using an argon ion gun with 5 kV for 300 seconds, it is found that the shown binding energies are located at positions corresponding to that of feature binding energies. In addition, an integrated area can obtain a content ratio of the element of the whole material. The distribution of the element of different depths and the composition of the composite film can be obtained with an etching step of different etching times.

Figure 4:
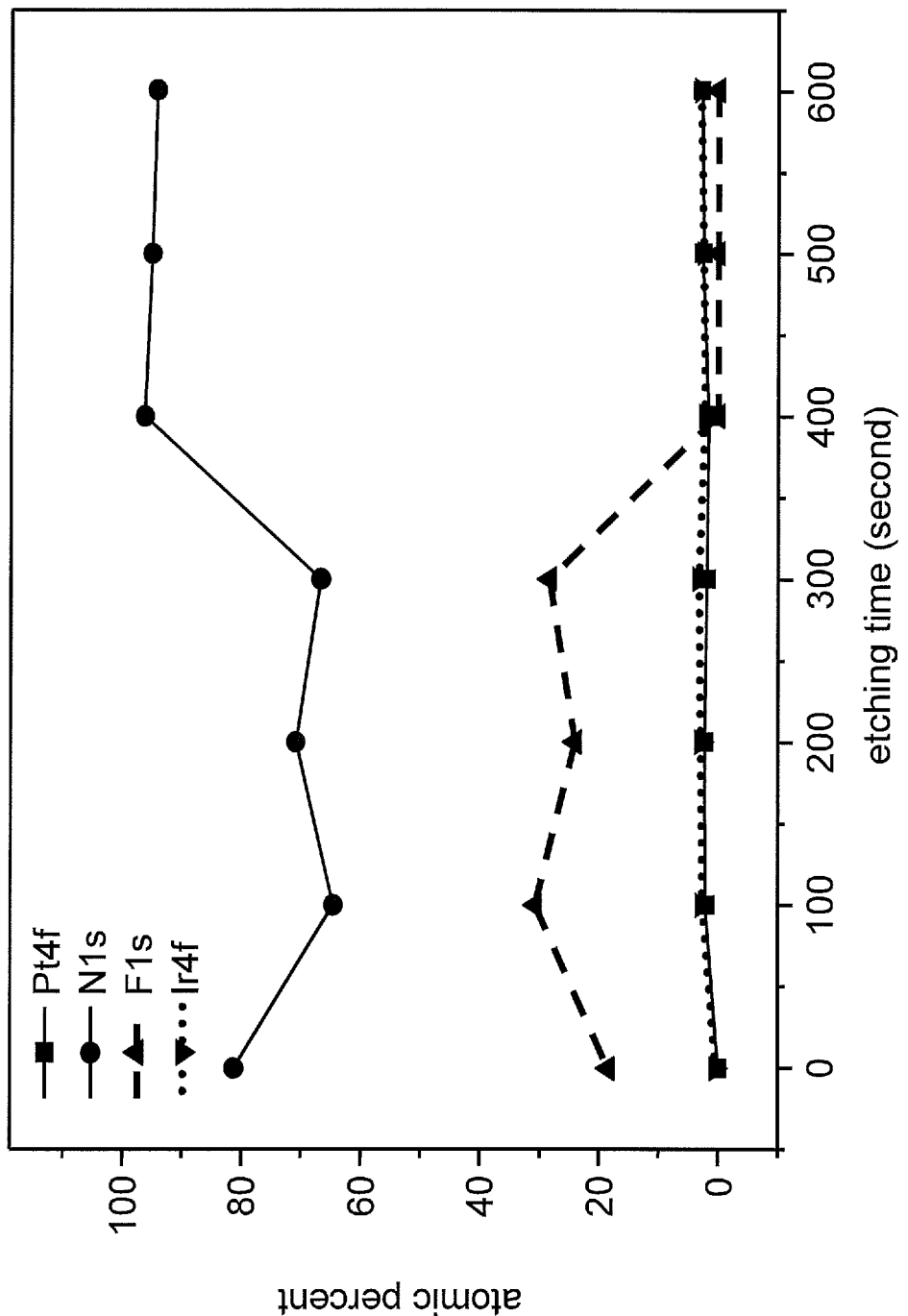
FIG. 4 shows depth profiles of the nano PtIr catalyst particles and the glucose oxidases on the surface of the Ir-mini sensor obtained by the ESCA performing six etching steps by a 5 kV argon ion gun in which each of the etching steps uses an etching time of 100 s, for investigating the distributions of the elements of the layer modified by the electrophoresis. Pt and Ir represent the nano PtIr catalyst particles. N represents the glucose oxidases. F represents the Nafion.

FIG. 4 shows depth profiles of the nano PtIr catalyst particles and the glucose oxidases on the surface of the Ir-mini sensor obtained by the ESCA performing six etching steps by a 5 kV argon ion gun in which each of the etching steps uses an etching time of 100 s. The distribution of the elements of the composite film formed by the electrophoresis deposition (EPD) method can be investigated from the figure. Pt and Ir represent the nano PtIr catalyst particles. N represents the glucose oxidases. In addition, F represents Nafion. The whole composition of the catalyst/enzyme composite film can be understood from FIG. 4. It is observed that the composite film has a great part of N atoms which contributing from glucose oxides (GOD). It is supposed that the result is resulted from the glucose oxidases having an electrophoretic mobility higher than that of the nano PtIr catalyst particles having the Nafion covering the surfaces of which. From FIG. 4, it is also observed that the Nafion influences the deposition rate of the glucose oxidases. In the electrophoresis solution, the glucose oxidase and the Nafion all exhibit negative electricity. Thus, during the electrophoresis process, the glucose oxidase would compete with the Nafion to occupy the electrochemical active position of the electrode surface at the same time. For example, as the Nafion is deposited on the electrode surface, it prohibits the deposition of the glucose oxidase.

Figure 5:
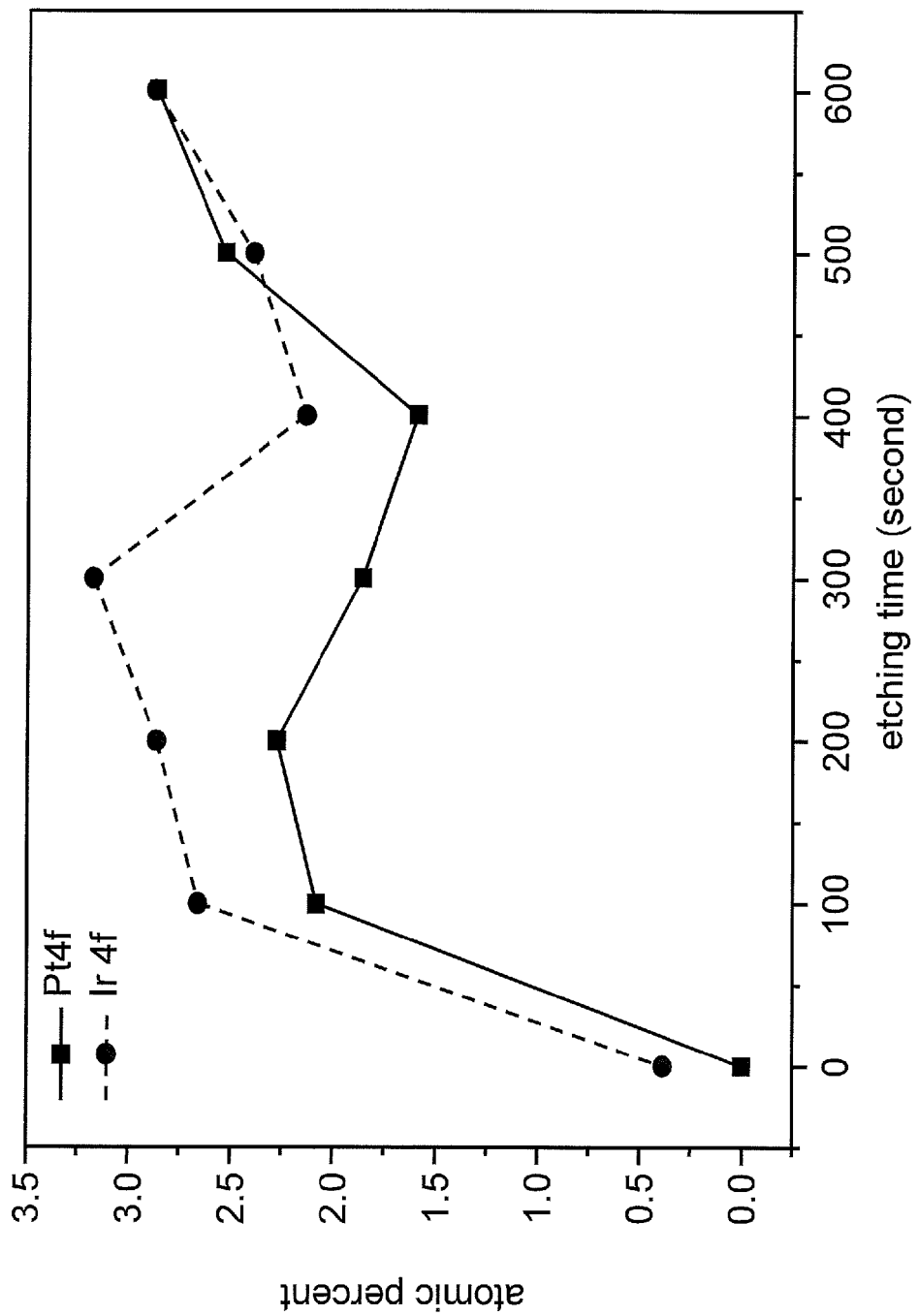
FIG. 5 is an enlarged view of FIG. 4 and shows depth profiles of the Pt and Ir measured by the ESCA.

The Pt and Ir compositions in the composite film can be observed clearly from FIG. 5, which is an enlarged view of FIG. 4 and shows depth profiles of the Pt and Ir measured by the ESCA. In FIG. 5, the composite film has a steady composition distribution except the surface composition is not homogeneous slightly (which may be resulted from a metal signal from the surface weaker than a metal signal from the inner of the composite film having the glucose oxidases in the electrophoresis solution covering the surface of which). Therefore, it is shown that the nano PtIr catalyst particles deposited by the electrophoresis method would provide a stable homogeneous structure which would benefit simultaneously forming the glucose oxidases stably deposited on the surface by the electrophoresis deposition (EPD) method. From FIG. 4 and FIG. 5, it is observed longitudinal-direction composition distribution of the electrode is quite homogeneous. Therefore, it is proved that the homogeneously-structured catalyst/enzyme composite film is formed on the surface of the electrode by this method.

C2: Electrochemical Characteristic Analysis for Mini Sensor Having Nano PtIr Catalyst Particles and Glucose Oxidases Simultaneously Deposited In embodiments, many kinds of electrochemical characteristic analyses for the mini sensor having the nano PtIr catalyst particles and the glucose oxidases simultaneously deposited, such as linear detecting range, limit of detection (LOD), interference test, reproducibility and stability for the mini sensor, catalysis reaction dynamics for the enzyme and stability for the mini sensor could be conducted. Partial experimental results are described below.

In embodiments, some experiments for the mini sensor (EPD-PtIr+GOD-Ir-mini sensor) having the nano PtIr catalyst particles and the glucose oxidases simultaneously deposited are made. An applied potential to the glucose may be detected preferably. From a cyclic voltammetry (CV) diagram of a phosphate buffered saline (PBS) solution having different glucose concentrations measured by EPD-PtIr+GOD-Ir-mini sensor with a scanning range of −0.4 V to 0.4 V (vs. Printed Ag/Ag/Cl), scanning rate of 50 mV/s and scanning number of 10, it is observed that at 0.2 V (vs. Printed Ag/AgCl), an oxidation current gradually increases with the increasing hydrogen peroxide concentration. At about −0.25 V (vs. Printed Ag/AgCl), a reduction current gradually increases with the increasing hydrogen peroxide concentration. From the cyclic voltammetry (CV) diagram of a phosphate buffered saline (PBS) solution having different glucose concentrations measured by EPD-PtIr+GOD-Ir-mini sensor with a scanning range of −0.4 V to 0.4 V (vs. Printed Ag/Ag/Cl), scanning rate of 50 mV/s and scanning number of 10, it is observed that the oxidation current increases with the increasing potential. It indicates a high applied potential would enhance the ability for detecting the glucose. However, human blood also contains other interferences having electrochemical activities. As the applied potential is high, an electric current signal noise would be generated due to a reaction of the interferences. Therefore, there is a need to find a proper detecting potential at which hydrogen peroxide generated from the oxidation of the glucose has good oxidation ability, and the reaction from the interferences can be avoided.

The following experiment discusses the optimum potential applied to the mini sensor having the nano PtIr catalyst particles and the glucose oxidases simultaneously deposited by the electrophoresis deposition (EPD) method for measuring the glucose concentration in the solution. The glucose sensing ability with different potentials is measured by an amperometric measurement method.

A conventional linear detecting range for sensing blood glucose of a diabetes patient is 3~12 mM. Therefore, a proper glucose linear detecting range is need for detecting the blood glucose precisely. From experiment results, it is found the optimum potential applied for measuring hydrogen peroxide is 0.3 V (vs. Printed Ag/AgCl). Next, the ability for sensing the glucose of different concentrations by using different potentials such as 0.3 V, 0.4 V and 0.5 V (vs. Printed Ag/AgCl). The results (of 3 sample quantity) obtained by recording one electric current value every 60 seconds are shown in FIG. 6, FIG. 7 and FIG. 8.

Figure 6:
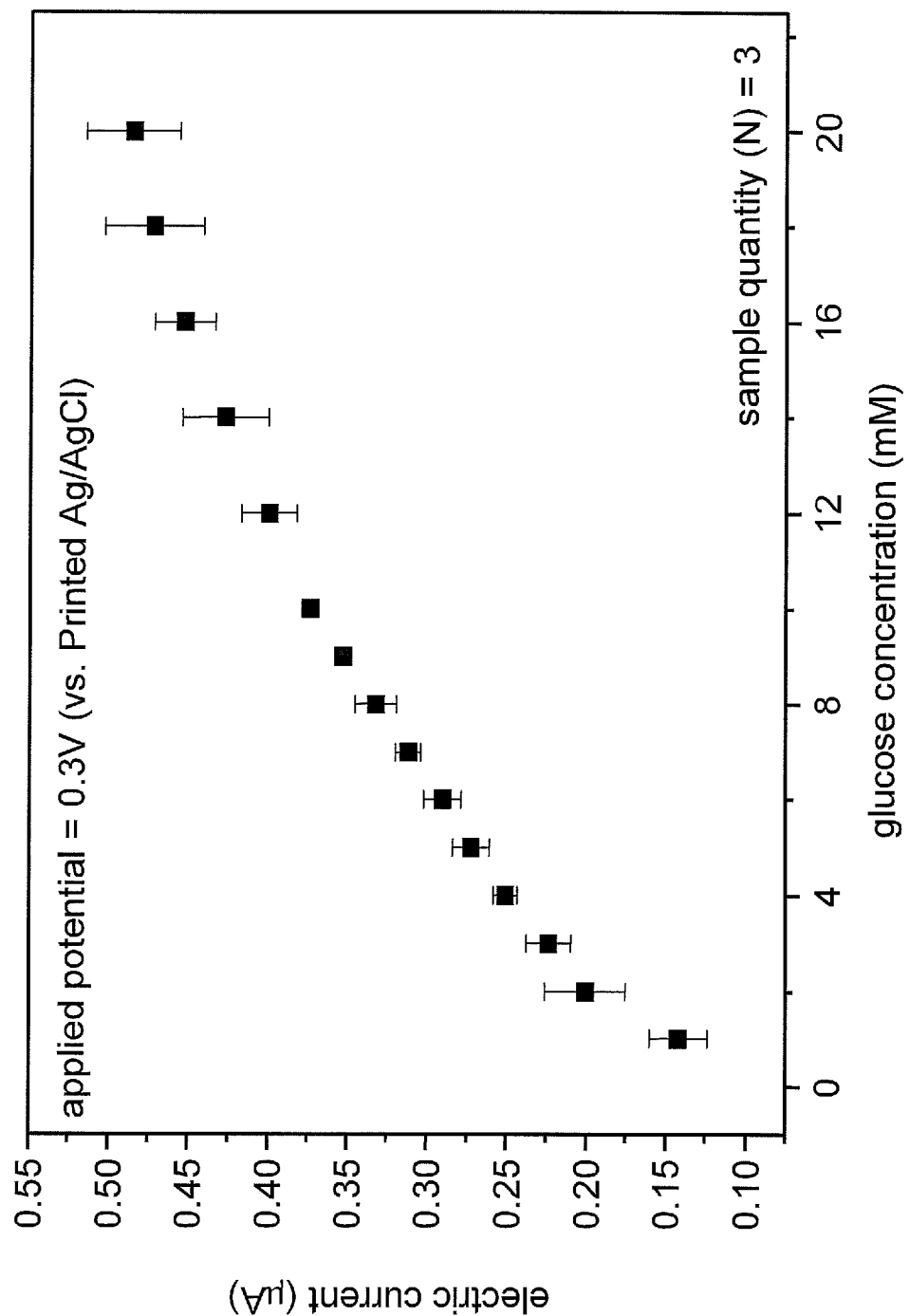
FIG. 6, FIG. 7 and FIG. 8 show results (of 3 sample quantity) of measured the electric currents and the abilities for sensing the glucose of the mini sensor under potentials of 0.3 V, 0.4 V and 0.5 V (vs. Printed Ag/AgCl), respectively, obtained by recording one electric current value every 60 seconds.
Figure 7:
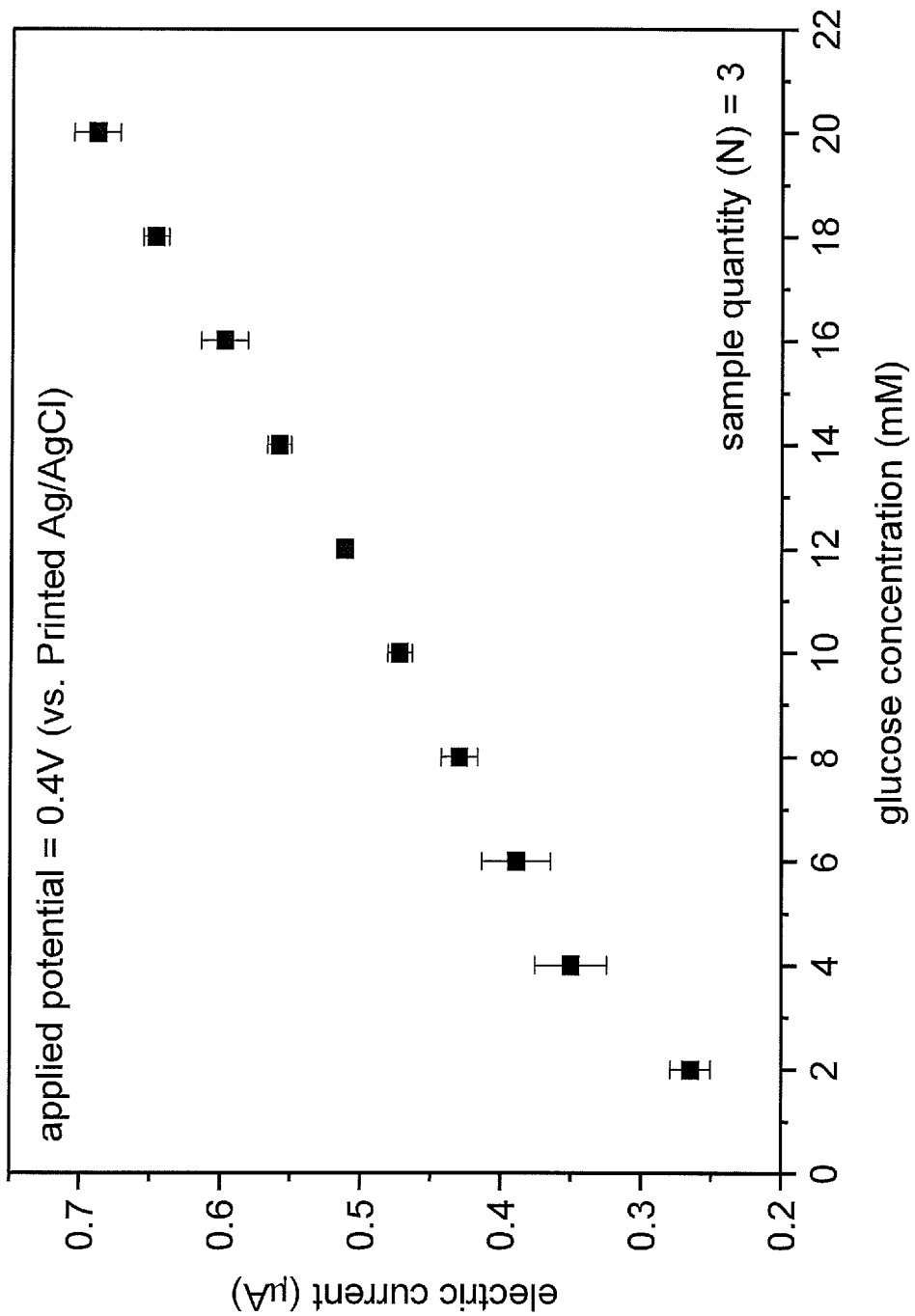
Figure 8:
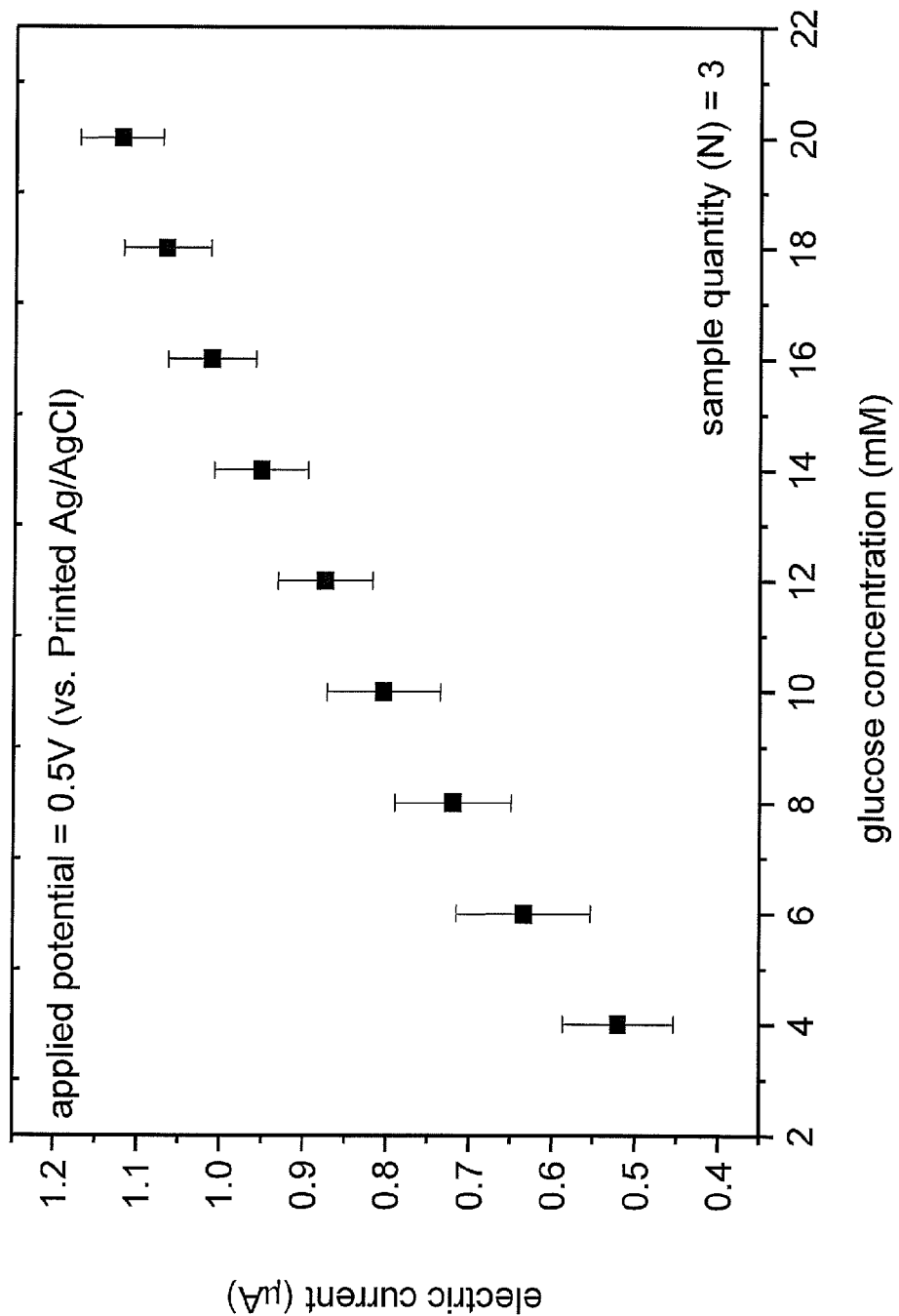

From FIG. 6 to FIG. 8, it is observed the glucose detecting linear range would change with different applied potentials. In FIG. 6, the glucose detecting linear range is 2-12 mM as applying 0.3 V (vs. Printed Ag/AgCl). In FIG. 7, the glucose detecting linear range is 2-20 mM as applying 0.4 V (vs. Printed Ag/AgCl). In FIG. 8, the glucose detecting linear range is 4-20 mM as applying 0.5 V (vs. Printed Ag/AgCl). It is observed that the linear range obtained by using 0.4 V (vs. Printed Ag/AgCl) is broader than that obtained by using 0.3 V (vs. Printed Ag/AgCl). In addition, the deviation value of the glucose sensing by using 0.5 V (vs. Printed Ag/AgCl) is higher then that by using 0.4 V and 0.3 V (vs. Printed Ag/AgCl), respectively. It may be resulted from the subsidiary reaction occurring at the electrode surface.

Figure 9:
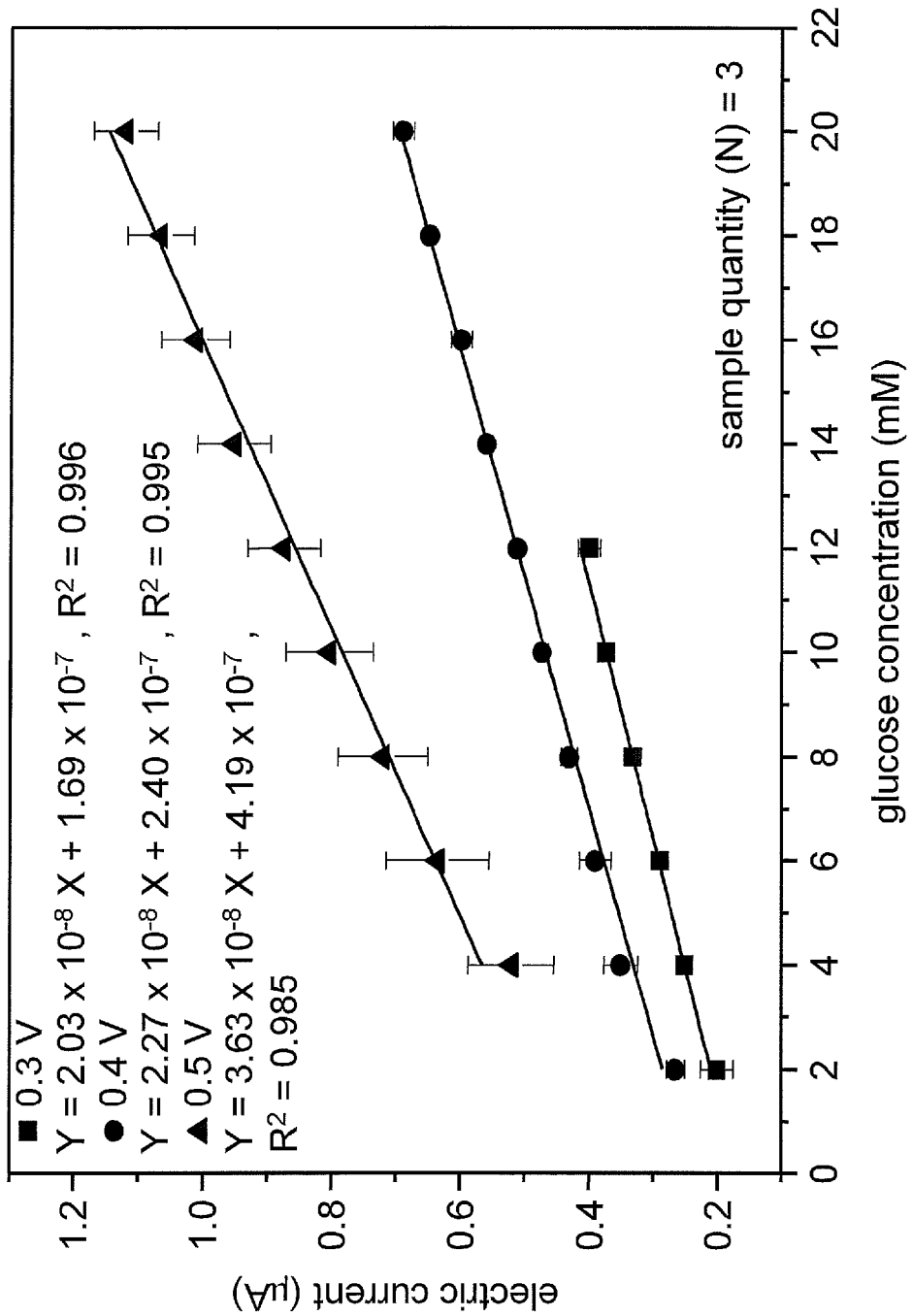
FIG. 9 is a diagram showing relationships between the oxidation current and the glucose concentration by using the EPD-PtIr+GOD-Ir-mini sensor with different potentials 0.3 V, 0.4 V and 0.5 V in the linear range. The working solution is 0.01 M phosphate buffered saline (PBS) solution (pH=7.4). The electric current values are measured once every 60 seconds.

FIG. 9 is a diagram showing relationships between the oxidation current and the glucose concentration by using the EPD-PtIr+GOD-Ir-mini sensor with different potentials 0.3 V, 0.4 V and 0.5 V in the linear range. The working solution is 0.01 M phosphate buffered saline (PBS) solution (pH=7.4). The electric current value is recorded every 60 seconds. The sensitivity for sensing the glucose and the linear correlation $R^2$ of the calibration obtained by the EPD-PtIr-Ir-mini sensor using different potentials are shown in table 1.

TABLE 1

| Potential (V vs. Printed Ag/AgCl) | Glucose Sensitivity (µA/mM)[a] | Linear correlation ($R^2$) |
|---|---|---|
| 0.3 V[b] | $2.03 \times 10^{-2}$ | 0.996 |
| 0.4 V[b] | $2.27 \times 10^{-2}$ | 0.995 |
| 0.5 V[b] | $3.63 \times 10^{-2}$ | 0.985 |

[a]Temperature: 25° C.(±1° C.)
[b]Electrophoresis deposition (EPD)parameters: a potentiostatic method using 0.5 V and 5 minutes of depositing time
Slurry parameters: 1 mg PtIr/C nano catalysts + 5 µL 5% Nafion 20 mg GOD homogeneously mixed and distributed in 1 mL 0.01M phosphate buffered saline (PBS) solution
[c]Sample quantity = 3

From FIG. 9, it is observed that the ability for sensing the glucose would, as well as the sensitivity of sensing hydrogen peroxide, increase as the applied potential arises. The gap between results obtained by using 0.4 V and 0.5 V (vs. Printed Ag/AgCl) is very big (about $1.4 \times 10^{-8}$ A/mM). The sensitivity of sensing the glucose is high as 0.5 V (vs. Printed Ag/AgCl) is applied. However, the mini sensor would have a big deviation as using a high potential.

Therefore, it is observed that using 0.4 V (vs. Printed Ag/AgCl) could obtain the optimum glucose detecting linear range (2 mM-20 mM) and the low deviation value.

The following embodiments discuss experiments and investigations relating to interference test, limiting of detection (LOD) and reproducibility, using potentials of 0.3 V and 0.4V (vs. Printed Ag/AgCl), respectively.

Interference Test

For a conventional glucose biosensor, an ascorbic acid (AA) and a uric acid (UA) are two kinds of common electroactive interferences in human blood. If the applied potential were excessively high, the current signal interference would occur due to the reaction of the interference. Therefore, there is a need to find a proper detecting potential at which hydrogen peroxide generated from the oxidation of the glucose has good oxidation ability, and the reaction of the interferences can be avoided.

According to public literatures, the average content of the ascorbic acid in normal human blood is about 0.4-0.6 mg/dL. In addition, the average content of the uric acid in human blood is about 3.5~7.2 mg/dL for a male adult and about 2.6~6.0 mg/dL for a female adult. In the interference test experiments of embodiments, the concentrations of the ascorbic acid and the uric acid, 1.5 mg/dL and 8 mg/dL respectively, are slightly higher than the average concentrations. In the experiment, the electric current signal of the solution having 5 mM glucose is measured. Next, a proper amount of the ascorbic acid or the uric acid is added into the solution. Thus, the influence to the electric current signal from the interference in the solution having the proper glucose concentration can be observed.

Figure 10A:
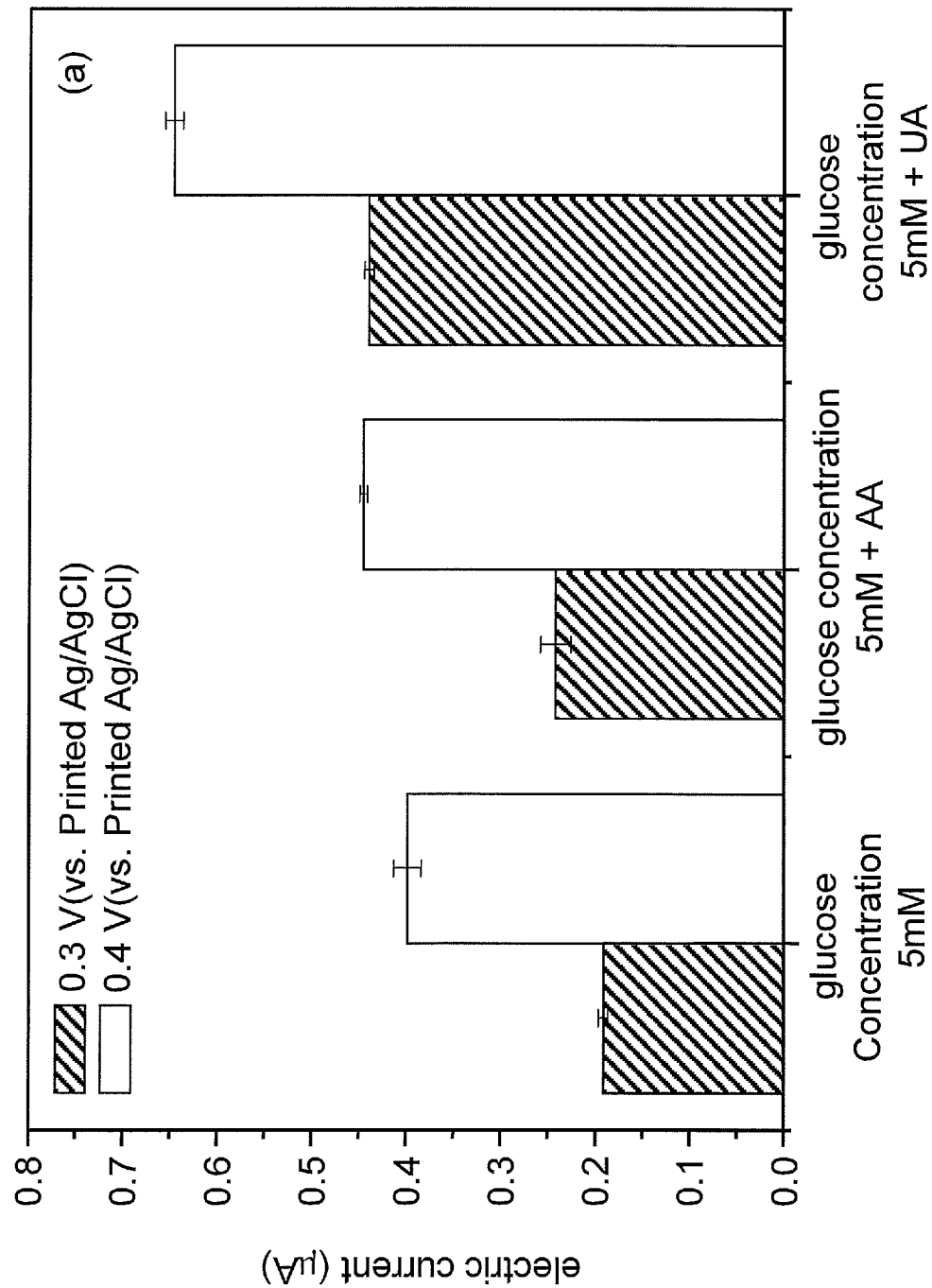
FIG. 10A and FIG. 10B are diagrams respectively showing electric current conditions of the 5 mM glucose solution, 5 mM glucose+1.5 mg/dL ascorbic acid solution, and 5 mM glucose+8 mg/dL uric acid solution (with sample quantity=3), measured by using the mini sensor having the nano PtIr catalyst particles and the glucose oxidases simultaneously deposited by the electrophoresis deposition (EPD) method with applying 0.3 V and 0.4 V (vs. Printed Ag/AgCl). The longitudinal axis shown in FIG. 10A
Figure 10B:
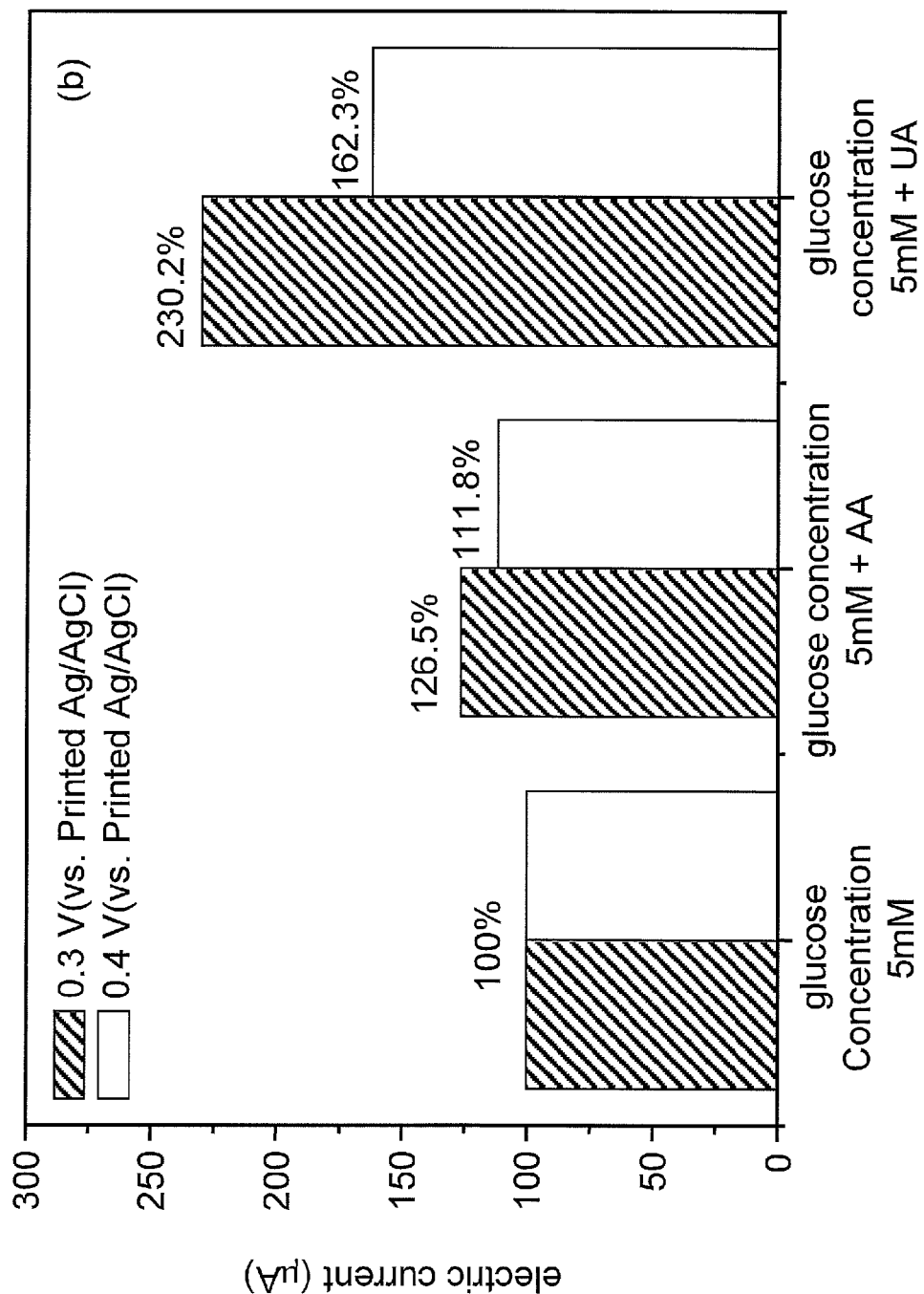

FIG. 10A and FIG. 10B are diagrams respectively showing electric current conditions of the 5 mM glucose solution, 5 mM glucose+1.5 mg/dL ascorbic acid solution, and 5 mM glucose+8 mg/dL uric acid solution (with sample quantity=3), measured by using the mini sensor having the nano PtIr catalyst particles and the glucose oxidases simultaneously deposited by the electrophoresis deposition (EPD) method with applying 0.3 V and 0.4 V (vs. Printed Ag/AgCl). The longitudinal axis shown in FIG. 10A represents the measured electric current for the solutions. The longitudinal axis shown in FIG. 10B represents the ratio of the measured electric current for the solution to the 5 mM glucose solution.

FIG. 10A and FIG. 10B show that the influence of the electric current of the interference under a potential of 0.4 V (vs. Printed Ag/AgCl) is weaker than that under a potential of 0.3 V (vs. Printed Ag/AgCl). Conventionally, the higher potential is, the more serious influence of the interference is. However, contrary to the conventional condition, the result of the experiment in this section shows that the selectivity of the device under the higher potential is better than that under the lower potential. It is presumed that the oxidation current is small since the low potential is not enough for catalyzing hydrogen peroxide. Therefore, the influence of the interference is severe. On the contrary, the ability for catalyzing hydrogen peroxide increases, as the applied potential is high. Therefore, the electric current response of the glucose increases. In addition, the interferences of the ascorbic acid and the uric acid are reduced since the electric current responses of the ascorbic acid and the uric acid are restricted. Thus, from the result of the interference test, it is proved that, in embodiments, the mini sensor has a good performance under the applied potential of 0.4 V (vs. Printed Ag/AgCl).

Limit of Detection (LOD) of Detecting Glucose of Mini Sensor

In the embodiments, the limit of detection (LOD) of the mini sensor having the nano PtIr catalyst particles and the glucose oxidases simultaneously deposited thereon by the electrophoresis deposition (EPD) method is tested.

Figure 11:
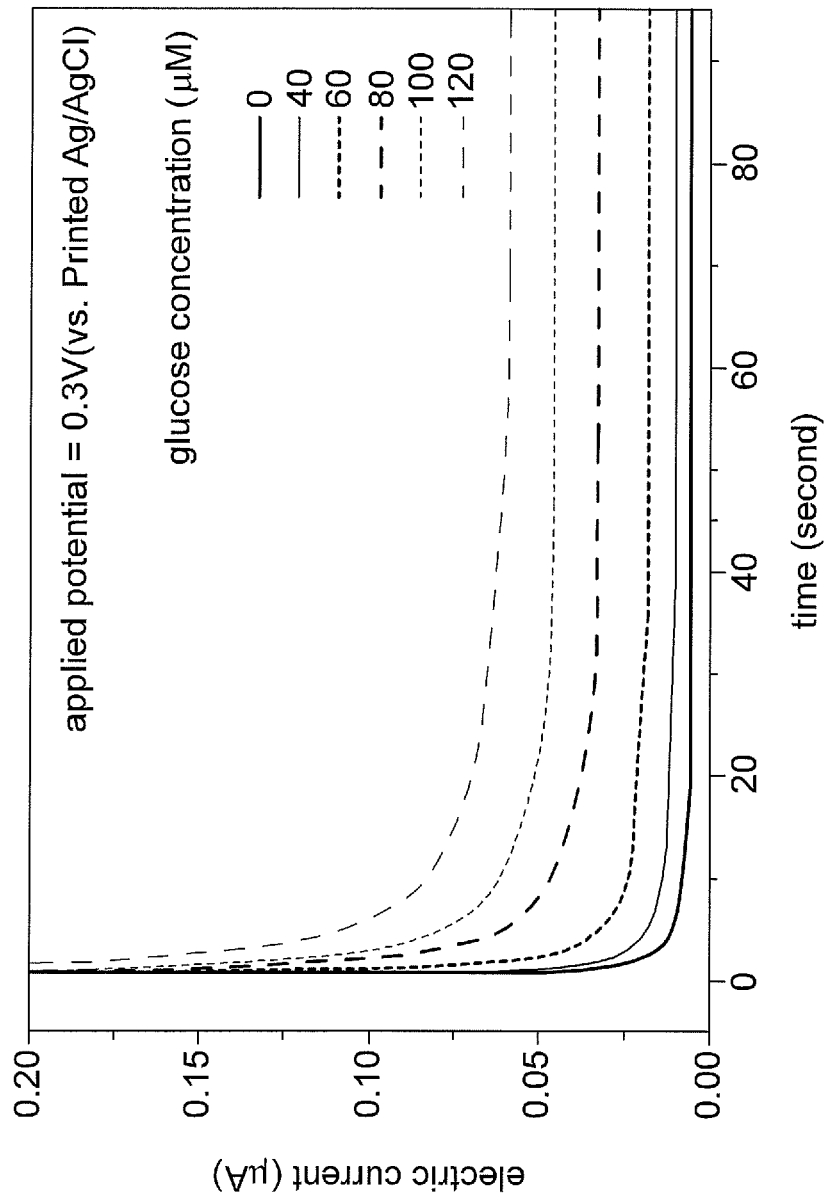
FIG. 11 and FIG. 12 show electric current-time curves of the EPD-PtIr+GOD-Ir-mini sensor under 0.3 V and 0.4 V (vs. Printed Ag/AgCl), respectively. The range of the concentration of the glucose is 0 μM~200 μM. In addition, the working solution is a phosphate buffered saline (PBS) solution of 0.01 M (pH=7.4).
Figure 12:
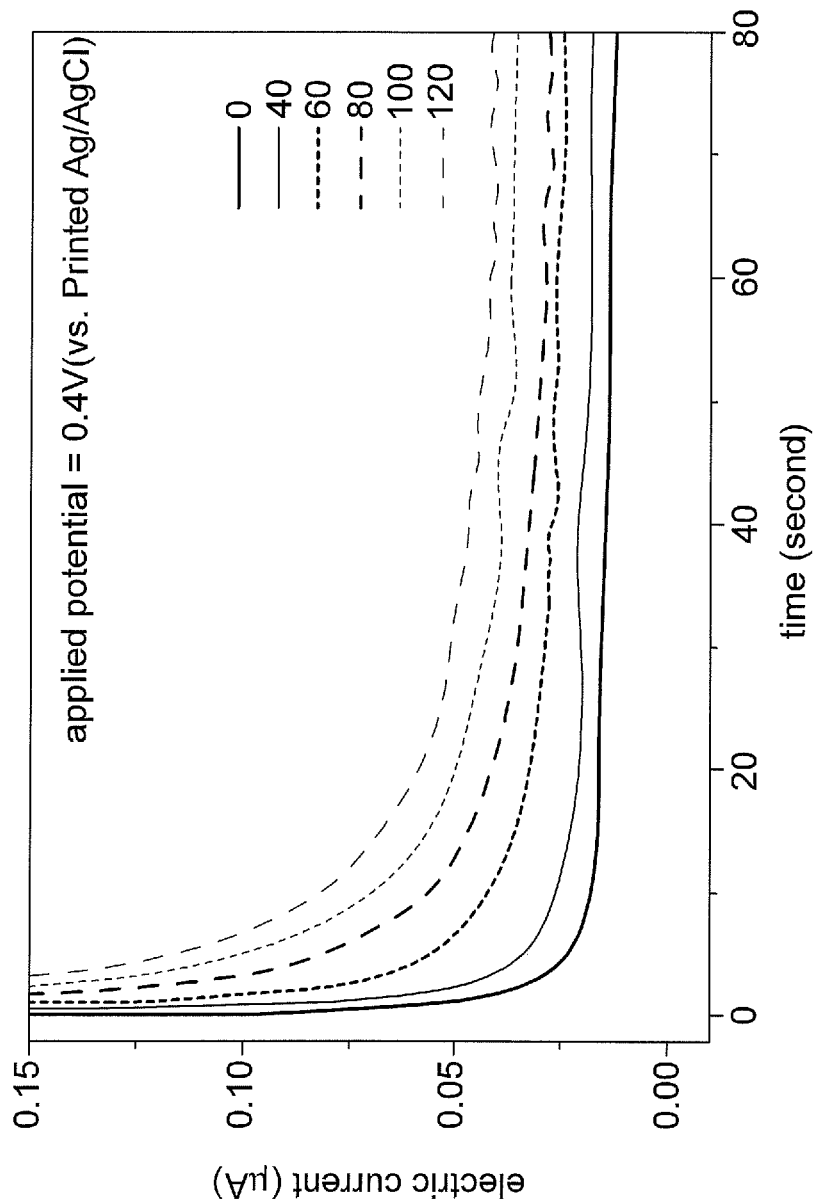

FIG. 11 and FIG. 12 show electric current-time curves of the EPD-PtIr+GOD-Ir-mini sensor under 0.3 V and 0.4 V (vs. Printed Ag/AgCl), respectively. The range of the concentration of the glucose is 0 μM-200 μM. In addition, the working solution is a phosphate buffered saline (PBS) solution of 0.01 M (pH=7.4). In experiments, after the glucoses of different concentrations are added into the solution, the minimum effective signals are calculated according to FIG. 11 and FIG. 12. If the signal/noise (S/N) is bigger than 3, the signal would be an effective signal. Otherwise, If the signal/noise (S/N) is smaller than 3, the signal would be an ineffective signal. Therefore, from figures, it is obtained that the minimum limits of detection with the applied potentials of 0.3 V and 0.4 V (vs. Printed Ag/AgCl) are 80 μm and 100 μm, respectively. It may be resulted from a high background current signal induced by applying the high potential. Thus, in the solution of low concentration, the signal/noise (S/N) obtained with the lower potential is larger than that with the higher potential.

Reproducibility and Stability of Mini Sensor

A desired biosensor can provide a user detecting results with high accuracy and good reproducibility. The word "reproducibility" means the ability of obtaining the same results under different conditions such as people operating the instrument, instruments, times, etc. If the mini sensor has a good reproducibility, it indicates the process condition of manufacturing the mini sensor is quite stable. Thus, the process condition can improve the yield of the mini sensor. Moreover, the reliability of the signal obtained from the mini sensor is improved. The word "repeatability" means the ability of obtaining the same results under the same condition. If the mini sensor has a good repeatability, it indicates the mini sensor manufactured by the electrophoresis deposition (EPD) method can be used repeatedly. In addition, the catalyst and the enzyme deposited by the electrophoresis method can still have a stable structure during the processes of measuring and cleaning the electrode. In embodiments of the present disclosure, the reproducibility and repeatability of the mini sensor are tested.

Figure 13:
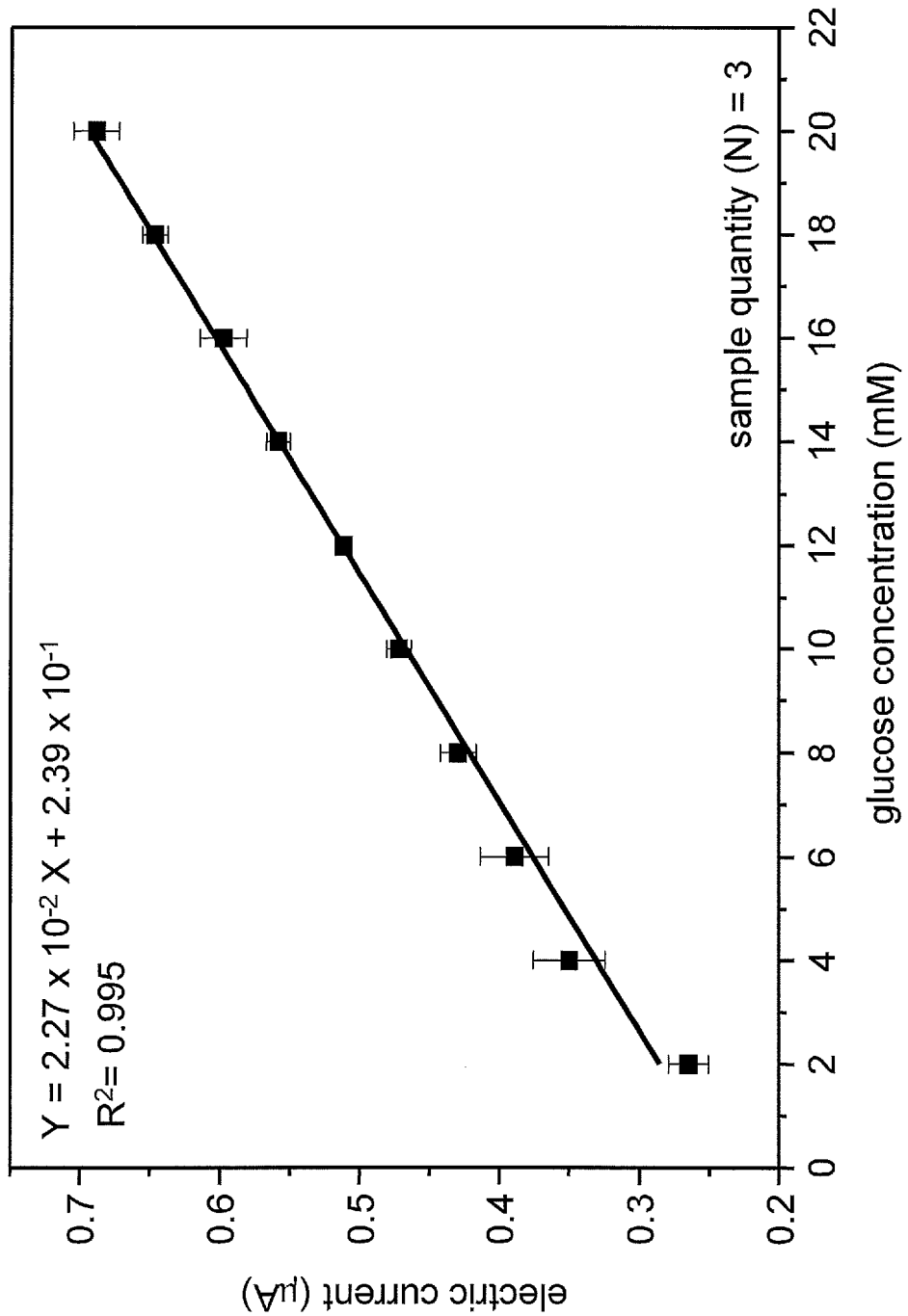
FIG. 13 presents electric current-time curves of a glucose of a concentration of 2 mM~20 mM obtained by a controlled potential analysis method using the EPD-PtIr+GOD-Ir-mini sensor under a potential of 0.4 V (vs. Printed Ag/AgCl). The working solution is a 0.01 M phosphate buffered saline (PBS) solution <pH=7.4>. Electric current values are measured once every 60 seconds.

FIG. 13 presents electric current-time curves of a glucose of a concentration of 2 mM-20 mM obtained by a controlled potential analysis method using the EPD-PtIr+GOD-Ir-mini sensor under a potential of 0.4 V (vs. Printed Ag/AgCl). The working solution is a 0.01 M phosphate buffered saline (PBS) solution <pH=7.4>. Electric current values are measured once every 60 seconds. The measurements are performed by different sets of the mini sensors. In this experiment, the degree of reproducibility is determined by measuring with the different sets of the mini sensors. FIG. 13 and table 2 show similar data, the relative standard deviation (RSD) of which is 7.14%, are obtained in the three measurements with different mini sensors. The data indicate the process of the electrophoresis deposition (EPD) method simultaneously depositing the nano PtIr catalyst particles and the glucose oxidases on the mini sensor is very stable and thus has a good reproducibility.

TABLE 2

| Glucose Conc. (mM) | Electric current (μA)[a] | | | | | |
| --- | --- | --- | --- | --- | --- | --- |
| | Sample-1[b] | Sample-2[b] | Sample-3[b] | Average | S.D.[c] | R.S.D.[c] |
| 2 | $2.51 \times 10^{-1}$ | $2.64 \times 10^{-1}$ | $2.80 \times 10^{-1}$ | $2.65 \times 10^{-1}$ | $1.44 \times 10^{-2}$ | 5.43% |
| 4 | $3.20 \times 10^{-1}$ | $3.64 \times 10^{-1}$ | $3.66 \times 10^{-1}$ | $3.50 \times 10^{-1}$ | $2.58 \times 10^{-2}$ | 7.37% |
| 6 | $3.61 \times 10^{-1}$ | $4.02 \times 10^{-1}$ | $4.04 \times 10^{-1}$ | $3.89 \times 10^{-1}$ | $2.44 \times 10^{-2}$ | 6.27% |
| 8 | $4.15 \times 10^{-1}$ | $4.35 \times 10^{-1}$ | $4.38 \times 10^{-1}$ | $4.30 \times 10^{-1}$ | $1.27 \times 10^{-2}$ | 2.96% |
| 10 | $4.63 \times 10^{-1}$ | $4.80 \times 10^{-1}$ | $4.73 \times 10^{-1}$ | $4.72 \times 10^{-1}$ | $8.69 \times 10^{-3}$ | 1.84% |
| 12 | $5.12 \times 10^{-1}$ | $5.14 \times 10^{-1}$ | $5.08 \times 10^{-1}$ | $5.12 \times 10^{-1}$ | $2.99 \times 10^{-3}$ | 0.58% |
| 14 | $5.68 \times 10^{-1}$ | $5.51 \times 10^{-1}$ | $5.56 \times 10^{-1}$ | $5.58 \times 10^{-1}$ | $8.41 \times 10^{-3}$ | 1.51% |
| 16 | $6.14 \times 10^{-1}$ | $5.81 \times 10^{-1}$ | $5.98 \times 10^{-1}$ | $5.98 \times 10^{-1}$ | $1.66 \times 10^{-2}$ | 2.78% |
| 18 | $6.56 \times 10^{-1}$ | $6.46 \times 10^{-1}$ | $6.38 \times 10^{-1}$ | $6.47 \times 10^{-1}$ | $9.22 \times 10^{-3}$ | 1.43% |
| 20 | $7.08 \times 10^{-1}$ | $6.81 \times 10^{-1}$ | $6.78 \times 10^{-1}$ | $6.89 \times 10^{-1}$ | $1.66 \times 10^{-2}$ | 2.41% |

[a]Temperature: 25° C.(±1° C.)
[b]Electrophoresis deposition (EPD) parameters: a potentiostatic method using 0.5 V and 5 minutes of depositing time
Slurry parameters: 1 mg PtIr/C nano catalysts + 5 μL 5% Nafion + 20 mg GOD homogeneously mixed and distributed in 2 mL 0.01M phosphate buffered saline (PBS) solution
[c]Sample quantity = 3

Table 3 shows results of the glucose of the concentration of 5 mM by the controlled potential analysis method using the EPD-PtIr+GOD-Ir-mini sensor with the applied potential of 0.4 V (vs. Printed Ag/AgCl). In this experiment, the degree of repeatability is determined by measuring the glucose three times using the same set of the mini sensor. Table 3 shows similar data, the relative standard deviation (RSD) of which is 7.16%, are obtained in the three measurements. The data indicate the mini sensor having the nano PtIr catalyst particles and the glucose oxidases fabricated by the electrophoresis deposition (EPD) method could have a good repeatability. It indicates the nano PtIr catalyst particles and the glucose oxidases simultaneously deposited on the working electrode of the mini sensor by the electrophoresis deposition (EPD) method could have a fine catalyst/enzyme composite structure fixed on the surface of the electrode stably.

TABLE 3

| | Electric current (μA)[a] | | | | | |
|---|---|---|---|---|---|---|
| Sample[b] | Run-1[a] | Run-2[a] | Run-3[a] | average | S.D.[c] | R.S.D.[c] |
| Glucose Conc. (mM) | $3.94 \times 10^{-1}$ | $3.98 \times 10^{-1}$ | $3.49 \times 10^{-1}$ | $3.80 \times 10^{-1}$ | $2.72 \times 10^{-2}$ | 7.16% |

[a]Temperature: 25° C.(±1° C.)
[b]Electrophoresis deposition (EPD) parameters: a potentiostatic method using 0.5 V and 5 minutes of depositing time
Slurry parameters: 1 mg PtIr/C nano catalysts + 5 μL 5% Nafion + 20 m GOD homogeneously mixed and distributed in 2 mL 0.01M phosphate buffered saline (PBS) solution
[c]The same mini sensor Dynamics of Catalysis Reaction of Enzyme The catalysis reaction of the enzyme usually can be described using the mechanism proposed by Michaelis-Menten, shown as the equation (2-2):

$$I = \frac{I_{Max} g C}{K_M^{app} + C} \quad (2\text{-}2)$$

I represents the response electric current (A) of the glucose. $I_{Max}$ represents the theoretical maximum response electric current (A) of the receptor. $K_M^{app}$ represents the Michaelis constant (M). C represents the concentration of the glucose of the solution to be tested (M).

An affinity between the test compound and the enzyme is represented by a $K_M^{app}$ value (Michaelis constant). A low $K_M^{app}$ value represents that the reaction has a high affinity. If the concentration ([C]) of the test compound is far smaller than the $K_M^{app}$, the reaction rate is proportioned to the concentration of the test compound (first order reaction). If the concentration of the test compound is far larger than the $K_M^{app}$, the reaction is a zero order reaction in which the rate is irrelevant to the concentration of the test compound. The $K_M^{app}$ and the $I_{Max}$ can be determined by using the Lineweaver-Burk equation (2-3) shown as below:

$$\frac{1}{I} = \frac{1}{I_{Max}} + \frac{K_M^{app}}{I_{Max}} \cdot \frac{1}{C} \quad (2\text{-}3)$$

I represents the response electric current of the glucose (A). $I_{Max}$ represents the theoretical maximum response electric current of the receptor (A). $K_M^{app}$ represents Michaelis constant (M). C represents the concentration of glucose of the solution to be tested (M).

Figure 14:
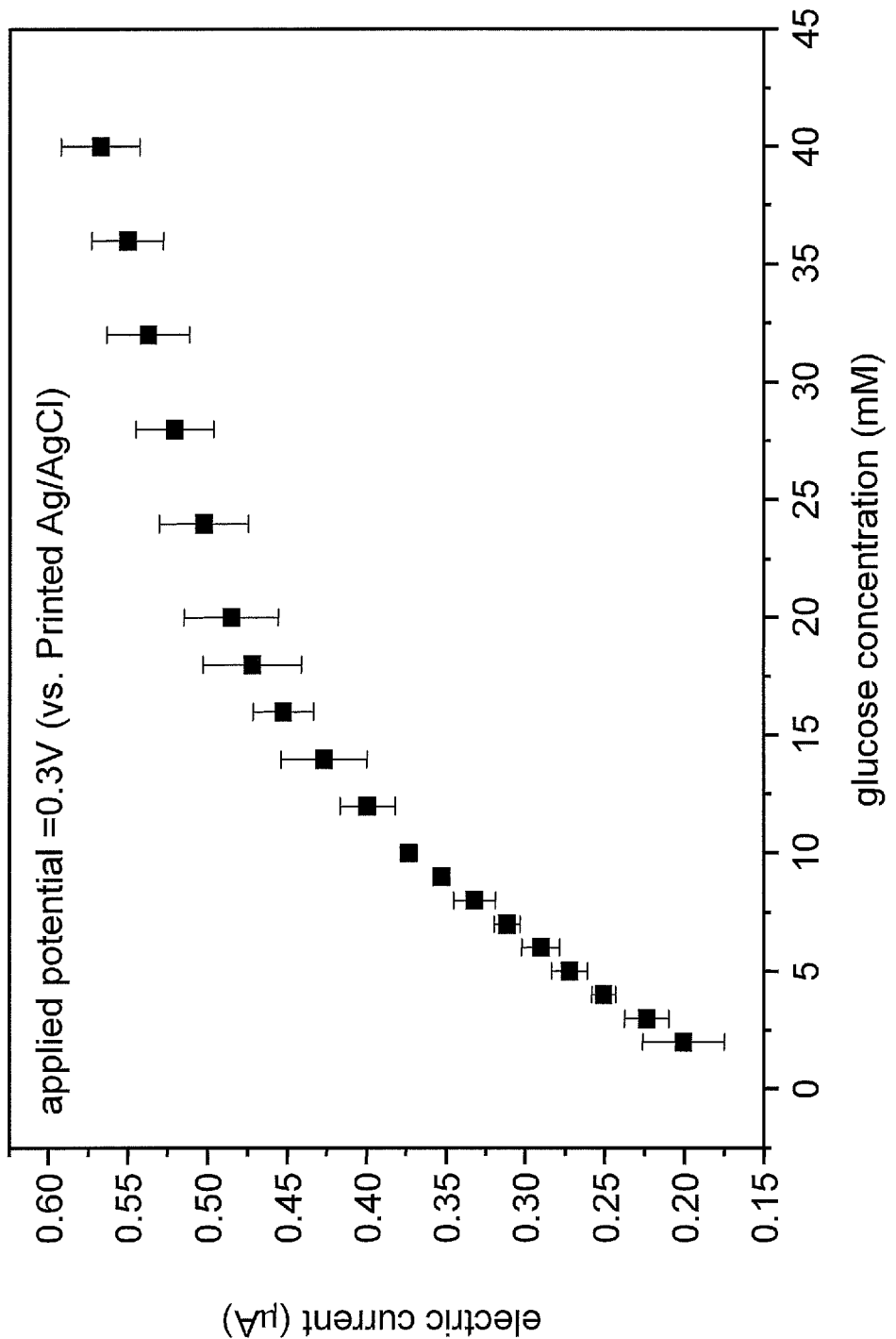
FIG. 14 presents electric current-time curves of a glucose of a concentration of 2 mM~40 mM obtained by a controlled potential analysis method using the EPD-PtIr+GOD-Ir-mini sensor under a potential of 0.3 V (vs. Printed Ag/AgCl). Electric current values are measured once every 60 seconds.

Parameters of the biosensor can be determined by using diagrams obtained by using the Lineweaver-Burk equation (2-3) in which I and C are respectively substituted by the electric current (I) and the measured concentration (C) in FIG. 14 obtained in the experiments. If the detecting region of the receptor is within the controlled dynamics region of the enzyme, the diagram illustrated by using the Lineweaver-Burk equation would be a linear line. Then, the $K_M^{app}$ and the $I_{max}$ of the receptor can be determined from the slope ($K_M^{app}/I_{Max}$) and the intercept ($1/I_{Max}$) of the linear line.

FIG. 14 presents electric current-time curves of a glucose of a concentration of 2 mM-40 mM obtained by a controlled potential analysis method using the EPD-PtIr+GOD-Ir-mini sensor under a potential of 0.3 V (vs. Printed Ag/AgCl). Electric current values are measured once every 60 seconds. In FIG. 14, the diagram obtained by measuring the glucose of the high concentration by suing the potential of 0.3 V (vs. Printed Ag/AgCl) exhibits as a non-linear curved line. It represents the reaction determining the rate with the concentration range is the enzyme kinetic controlled reaction.

Figure 15:
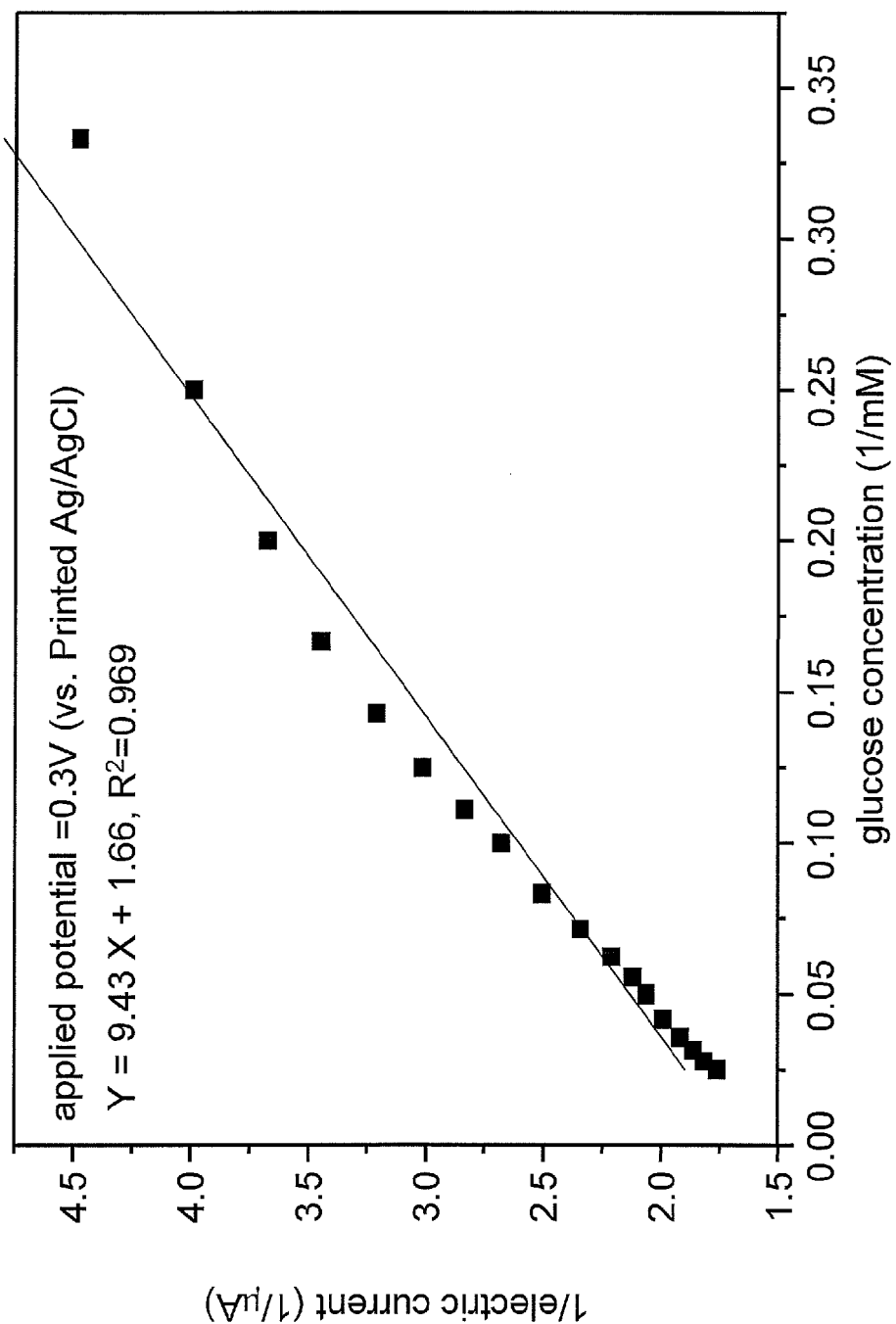
FIG. 15 is diagramed by using the reciprocals of the response electric currents and the concentrations of the test compounds in FIG. 14. The $K_M^{app}$ and the $I_{Max}$ of the mini sensor having the nano PtIr catalyst particles and the glucose oxidases deposited by the electrophoresis deposition (EPD) method can be obtained by using the Lineweaver-Burk equation.

FIG. 15 is diagramed by using the reciprocals of the response electric currents and the concentrations of the test compounds in FIG. 14. From the Lineweaver-Burk equation (equation (2-3), linear equation), it is obtained that the $K_M^{app}$ and the $1_{max}$ of the mini sensor having the nano PtIr catalyst particles and the glucose oxidases deposited by the electrophoresis deposition (EPD) method are 5.68 mM and 6.02× $10^{-7}$ A, respectively. It is found that the mini sensor having the nano PtIr catalyst particles and the glucose oxidases deposited by the electrophoresis deposition (EPD) method has the pretty low $K_M^{app}$ as compared with other references known in the art. It represents that the enzyme in the composite catalyst/enzyme homogeneously structured layer formed by the electrophoresis deposition (EPD) has high activity and affinity with the glucose.

Preservation Test of Mini Sensor

It is a challenge to improve the preservation of the biosensor for any kind of the bioreceptor effectively. Generally, for prolonging the preservation of the enzyme of the working electrode of the bioreceptor manufactured by the conventional immobilization method, in the conventional preservation method, the biosensor is placed in a condition of 4° C. Therefore, the activity of the enzyme on the surface of the electrode is prolonged. However, this preservation method has a disadvantage of decreasing portable convenience of the mini sensor dramatically.

Therefore, a mini biological sensor fitting in with practical habits of normal users is needed. In embodiments, the mini sensor is put in the clip-chain bag (zip bag) and then preserved at the room temperature for testing the long time preservation. The room temperature is about 25° C. (±1° C.).

Figure 16:
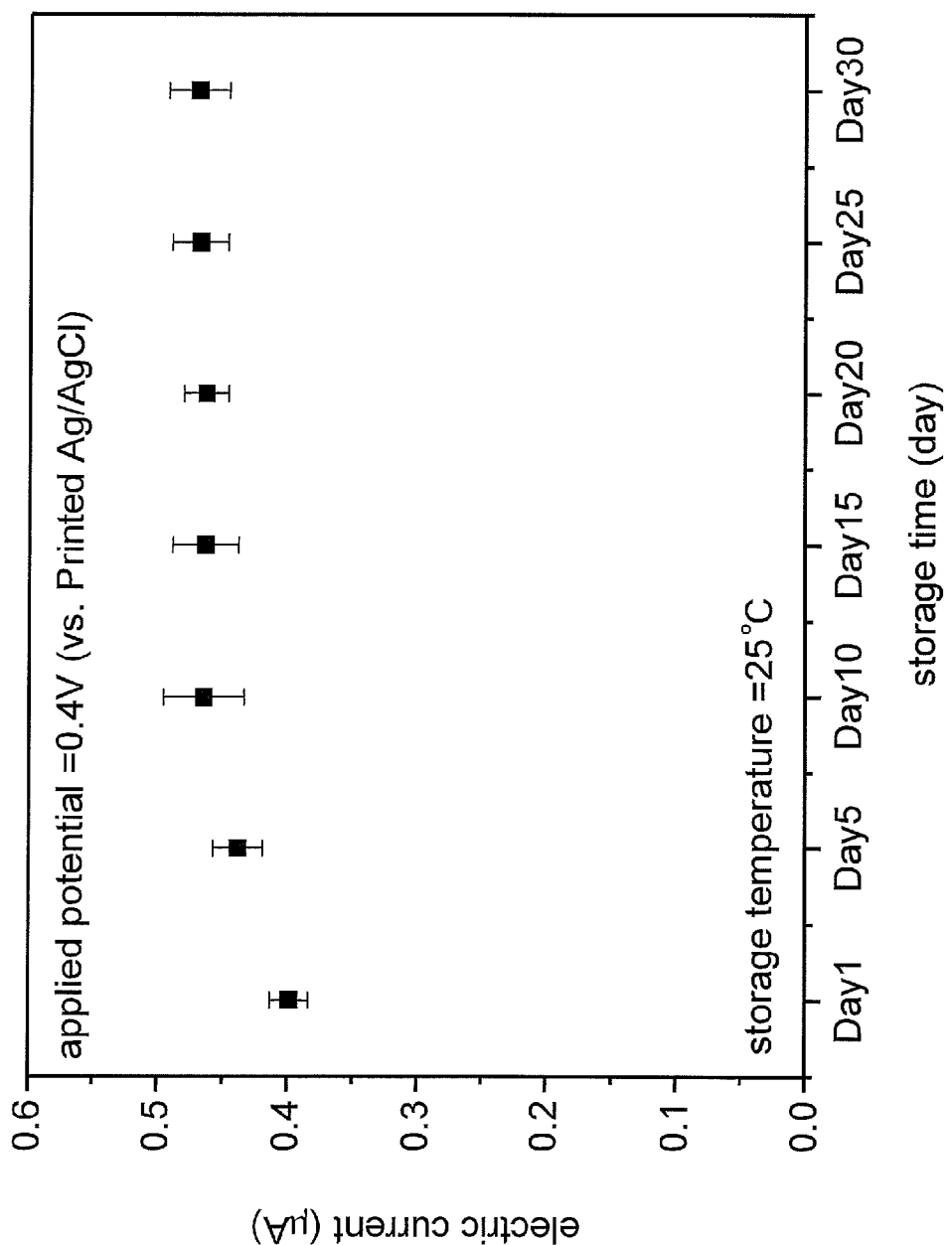
FIG. 16 shows longterm stability test results (of sample quantities of 3) of measured electric current signals of the 5 mM glucose solution by using the EPD-PtIr+GOD-Ir-mini sensor having different the preservation times.

During the experiments, the electric current signals (sample quantities=3) of the glucose solution in a concentration of 5 mM are measured by the EPD-PtIr+GOD-Ir-mini sensor which have been preserved for 1 day, 5 days, 10 days, 15 days, 20 days, 25 days and 30 days, respectively. FIG. 16 and table 4 show detail results of the preservation times and measured electric current signals.

TABLE 4

| | Electric current (μA)[a] | | | | | |
|---|---|---|---|---|---|---|
| Time (day) | Sample-1[b] | Sample-2[b] | Sample-3[b] | Average | S.D.[c] | R.S.D.[c] |
| 1 | $4.11 \times 10^{-1}$ | $3.82 \times 10^{-1}$ | $4.02 \times 10^{-1}$ | $3.98 \times 10^{-1}$ | $1.45 \times 10^{-2}$ | 3.64% |
| 5 | $4.20 \times 10^{-1}$ | $4.58 \times 10^{-1}$ | $4.34 \times 10^{-1}$ | $4.38 \times 10^{-1}$ | $1.91 \times 10^{-2}$ | 4.37% |
| 10 | $4.66 \times 10^{-1}$ | $4.33 \times 10^{-1}$ | $4.95 \times 10^{-1}$ | $4.65 \times 10^{-1}$ | $3.11 \times 10^{-2}$ | 6.70% |

TABLE 4-continued

| | Electric current (μA)[a] | | | | | |
|---|---|---|---|---|---|---|
| Time (day) | Sample-1[b] | Sample-2[b] | Sample-3[b] | Average | S.D.[c] | R.S.D.[c] |
| 15 | $4.34 \times 10^{-1}$ | $4.73 \times 10^{-1}$ | $4.82 \times 10^{-1}$ | $4.63 \times 10^{-1}$ | $2.55 \times 10^{-2}$ | 5.52% |
| 20 | $4.78 \times 10^{-1}$ | $4.44 \times 10^{-1}$ | $4.67 \times 10^{-1}$ | $4.63 \times 10^{-1}$ | $1.73 \times 10^{-1}$ | 3.73% |
| 25 | $4.42 \times 10^{-1}$ | $4.78 \times 10^{-1}$ | $4.82 \times 10^{-1}$ | $4.68 \times 10^{-1}$ | $2.20 \times 10^{-1}$ | 4.71% |
| 30 | $4.79 \times 10^{-1}$ | $4.42 \times 10^{-1}$ | $4.86 \times 10^{-1}$ | $4.69 \times 10^{-1}$ | $2.36 \times 10^{-1}$ | 5.04% |

[a]Temperature: 25° C.(±1° C.)
[b]Electrophoresis deposition (EPD) parameters: a potentiostatic method using 0.5 V and 5 minutes of depositing time
Slurry parameters: 1 mg PtIr/C nano catalysts + 5 μL 5% Nafion + 20 mg GOD homogeneously mixed and distributed in 2 mL 0.01M phosphate buffered saline (PBS) solution
[c]Sample quantity = 3

The current results show that the mini sensor having the nano PtIr catalyst particles and the glucose oxidases simultaneously deposited by the electrophoresis deposition (EPD) method could still have a stable ability of detecting the glucose after the long time preservation at the room temperature (about 25° C.). The reason of which is proposed the homogeneous composite catalyst/enzyme structure could provide a stable three-dimensional space composite structure environment. Therefore, the repeatability of the enzyme is improved. In addition, the preservation limit of the enzyme at the room temperature is prolonged.

Comprehensive Discussion

According to the above-mentioned embodiments, from the results of the many electrochemical characteristic analysis experiments and considering parameters of the electrophoresis solution and the conditions of the electrophoresis process of the mini sensor having the nano PtIr catalyst particles and the glucose oxidases deposited simultaneously by the electrophoresis deposition (EPD) method, it is found that: the extremely stable electrophoresis solution could be obtained by uniformly dispersing the 1 mg nano PtIr catalyst particles/mL, the 5 μL Nafion of 5%/mL and the 20 mg GOD/mL in the 0.01 M phosphate buffered saline (PBS) solution (pH=7.4). In addition, the mini biosensor having excellent efficiency for detecting the glucose could be fabricated by the potentiostatic method using the applied potential of 0.5 V (vs. Printed Ag/AgCl) and depositing time of 5 mins.

From the depth profile results of the ESCA, it is found that the composition distributions of the longitudinal direction of the electrode are very uniform. It proves that the homogeneously-structured composite catalyst/enzyme structure can be certainty formed on the surface of the electrode of the mini sensor. The homogeneously-structured composite catalyst/enzyme layer could provide a unique environment for shortening the path between hydrogen peroxide generated from the reaction of the test compound and the enzyme and the surface of the catalyst. In addition, the electron generated from the reaction of hydrogen peroxide and the surface of the catalyst could pass through the support of the nana metal catalyst rapidly to the substrate of the working electrode. This structure could improve improving the response signal and the sensitivity of the bioreceptor.

Form the reproducibility experiments, it is found that the process of electrophoresis deposition (EPD) method depositing the nano PtIr catalyst particles and the glucose oxidases simultaneously is very stable. The ability for sensing the glucose of the mini sensor having the nano PtIr catalyst particles and the glucose oxidases simultaneously deposited by the electrophoresis deposition (EPD) method using the optimum electrophoresis solution parameters and electrophoresis process conditions is increased by 1.25 times as compared with the conventional mini sensor having the merely glucose oxidases deposited by the electrophoresis deposition (EPD) method. This result indicates that the ability of sensing the glucose of the mini sensor is certainly improved by using the composite structure having the nano PtIr catalyst particles and the glucose oxidases in the embodiments.

From the results of experiments for investigating the enzyme dynamics, it is found the mini sensor having the nano PtIr catalyst particles and the glucose oxidases deposited by the electrophoresis deposition (EPD) method in the embodiments has the low Michaelis constant ($K_M^{app}$=5.68 mM in one embodiment) as compared with the other references known in the art. It indicates that the enzyme in the homogeneously-structured catalyst/enzyme composite layer formed by the electrophoresis deposition (EPD) has the high activity and affinity with the glucose. The reason of which is supposed that the homogeneously-structured catalyst/enzyme composite layer could provide a unique structure environment that could improve the stability of the enzyme and dramatically prolong the preservation of the bioreceptor. According to the results of the experiments, the preservation time at least at the room temperature is longer than 30 days.

Moreover, for the mini glucose biosensor fabricated by using the optimum electrophoresis deposition (EPD) parameters, under the applied potential of 0.4 V (vs. Printed Ag/AgCl), the detecting linear range of the glucose is 2 mM-20 mM. The Michaelis constant is 5.68 mM. The minimum limit of detection is 0.1 mM. In addition, the detecting sensitivity is 2.89 μA/mM·cm²($R^2$=0.995, R.S.D.=3.26%, N=3).

According, in the embodiments of the present disclosure, the homogeneously-structured catalyst/enzyme composite electrode is formed by depositing the catalyst particles, such as the nano PtIr catalyst particles, and the enzymes, such as the glucose oxidases simultaneously on the surface of the working electrode of the mini sensor by the electrophoresis deposition (EPD) method. Through the many experiments, for example, for analyzing the depth profile of the electrode structure by the ESCA, it is verified that the layer of the homogeneously-structured catalyst/enzyme composite film having the catalyst particles and the enzymes deposited by the electrophoresis deposition (EPD) method simultaneously can be preserved for the long time (longer than 30 days at the room temperature. The experiment results indicate that the mini sensor having the homogeneously-structured composite catalyst/enzyme structure fabricated by the method according to the present disclosure has high reproducibility, repeatability and accuracy.

While the disclosure has been described by way of example and in terms of the embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A catalyst-enzyme composite film structure, comprising:
   a plurality of catalyst supports; and
   a plurality of catalyst particles and enzymes homogeneously mixed and distributed, and the catalyst particles and enzymes formed on the catalyst supports, the catalyst particles catalyzing a biochemical reaction and the enzymes increasing a rate of an electrochemical reaction, wherein the enzymes and the catalyst particles are simultaneously deposited onto a surface of a substrate by an electrophoresis deposition (EPD) method.

2. The catalyst-enzyme composite film structure according to claim 1, wherein the enzymes for catalyzing the biochemical reaction react with a biomolecule to form hydrogen peroxide ($H_2O_2$).

3. The catalyst-enzyme composite film structure according to claim 2, wherein the enzymes are selected from a group consisting of a glucose oxidase (EC 1.1.3.4), a malate oxidase (EC 1.1.3.3), a hexose oxidase (EC 1.1.3.5), a cholesterol oxidase (EC 1.1.3.6), an aryl-alcohol oxidase (EC 1.1.3.7), a L-gulonolactone oxidase (EC 1.1.3.8), a galactose oxidase (EC 1.1.3.9), a pyranose oxidase (EC 1.1.3.10), a L-sorbose oxidase (EC 1.1.3.11), a pyridoxine 4-oxidase (EC 1.1.3.12), an alcohol oxidase (1.1.3.13), a (S)-2-hydroxy-acid oxidase (1.1.3.15), an ecdysone oxidase (EC 1.1.3.16), a choline oxidase (EC 1.1.3.17), a secondary-alcohol oxidase (EC 1.1.3.18), a 4-hydroxymandelate oxidase (EC 1.1.3.19), a long-chain-alcohol oxidase (EC 1.1.3.20), a glycerol-3-phosphate oxidase (EC 1.1.3.21), a thiamine oxidase (EC 1.1.3.23), a hydroxyphytanate oxidase (EC 1.1.3.27), an N-acylhexosamine oxidase (EC 1.1.3.29), a polyvinyl-alcohol oxidase (EC 1.1.3.30), a D-Arabinono-1,4-lactone oxidase (EC 1.1.3.37), a vanillyl-alcohol oxidase (EC 1.1.3.38), an nucleoside oxidase (H2O2-forming) (EC 1.1.3.39), a D-mannitol oxidase (EC 1.1.3.40), a xylitol oxidase (EC 1.1.3.41), a cellobiose dehydrogenase (acceptor) (EC 1.1.99.18), a formate dehydrogenase (EC 1.2.1.2), an aldehyde oxidase (EC 1.2.3.1), a pyruvate oxidase (EC 1.2.3.3), an oxalate oxidase (EC 1.2.3.4), a glyoxylate oxidase (EC 1.2.3.5), a pyruvate oxidase (CoA-acetylating) (EC 1.2.3.6), an aryl-aldehyde oxidase (EC 1.2.3.9), a retinal oxidase (EC 1.2.3.11), an abscisic-aldehyde oxidase (EC 1.2.3.14), an oxoglutarate dehydrogenase (succinyl-transferring) (EC 1.2.4.2), a dihydroorotate oxidase (EC 1.3.3.1), a coproporphyrinogen oxidase (EC 1.3.3.3), an acyl-CoA oxidase (EC 1.3.3.6), a dihydrouracil oxidase (EC 1.3.3.7), a tetrahydroberberine oxidase (EC 1.3.3.8), a tryptophan alpha,beta-oxidase (EC 1.3.3.10), a pyrroloquinoline-quinone synthase (EC 1.3.3.11), a L-galactonolactone oxidase (EC 1.3.3.12), an acyl-CoA dehydrogenase (EC 1.3.99.3), a dihydroorotate dehydrogenase (EC 1.3.99.11), a D-aspartate oxidase (EC 1.4.3.1), a L-amino-acid oxidase (EC 1.4.3.2), a D-amino-acid oxidase (EC 1.4.3.3), an amine oxidase (flavin-containing) (EC 1.4.3.4), a pyridoxal 5'-phosphate synthase (EC 1.4.3.5), an amine oxidase (copper-containing) (EC 1.4.3.6), a D-glutamate oxidase (EC 1.4.3.7), an ethanolamine oxidase (EC 1.4.3.8), a putrescine oxidase (EC 1.4.3.10), a L-glutamate oxidase (EC 1.4.3.11), a cyclohexylamine oxidase (EC 1.4.3.12), a protein-lysine 6-oxidase (EC 1.4.3.13), a L-lysine oxidase (EC 1.4.3.14), a D-glutamate (D-aspartate) oxidase (EC 1.4.3.15), a L-aspartate oxidase (EC 1.4.3.16), a glycine oxidase (EC 1.4.3.19), a L-lysine 6-oxidase (EC 1.4.3.20), an amine dehydrogenase (EC 1.4.99.3), a FMN reductase (EC 1.5.1.29), a sarcosine oxidase (EC 1.5.3.1), an N-methyl-L-amino-acid oxidase (EC 1.5.3.2), an N6-methyl-lysine oxidase (EC 1.5.3.4), (S)-6-hydroxynicotine oxidase (EC 1.5.3.5), a (R)-6-hydroxynicotine oxidase (EC 1.5.3.6), a L-pipecolate oxidase (EC 1.5.3.7), a dimethylglycine oxidase (EC 1.5.3.10), a polyamine oxidase (EC 1.5.3.11), a dihydrobenzophenanthridine oxidase (EC 1.5.3.12), a trimethylamine dehydrogenase (EC 1.5.8.2), a L-pipecolate dehydrogenase (EC 1.5.99.3), a cytokinin dehydrogenase (EC 1.5.99.12), an NAD(P)H oxidase (EC 1.6.3.1), an NAD(P)H dehydrogenase (quinone) (EC 1.6.5.2), an nitrite reductase (NO-forming) (EC 1.7.2.1), an nitroalkane oxidase (EC 1.7.3.1), an urate oxidase (EC 1.7.3.3), a 3-aci-nitropropanoate oxidase (EC 1.7.3.5), a dihydrolipoyl dehydrogenase (EC 1.8.1.4), a sulfite oxidase (EC 1.8.3.1), a thiol oxidase (EC 1.8.3.2), a glutathione oxidase (EC 1.8.3.3), a methanethiol oxidase (EC 1.8.3.4), a prenylcysteine oxidase(EC 1.8.3.5), a 3-hydroxyanthranilate oxidase (EC 1.10.3.5), a rifamycin-B oxidase (EC 1.10.3.6), an NADH peroxidase (EC 1.11.1.1), a 2-nitropropane dioxygenase (EC 1.13.11.32), a lysine 2-monooxygenase (EC 1.13.12.2), a lactate 2-monooxygenase (EC 1.13.12.4), a photinus-luciferin 4-monooxygenase (ATP-hydrolysing) (EC 1.13.12.7), a phenylalanine 2-monooxygenase (EC 1.13.12.9), a clavaminate synthase (EC 1.14.11.21), an naphthalene 1,2-dioxygenase (EC 1.14.12.12), a 4-aminobenzoate 1-monooxygenase (EC 1.14.13.27), an alkanal monooxygenase (FMN-linked) (EC 1.14.14.3), a phenylalanine 4-monooxygenase (1.14.16.1), an anthranilate 3-monooxygenase (EC 1.14.16.3), a monophenol monooxygenase (EC 1.14.18.1), a lathosterol oxidase (EC 1.14.21.6), a superoxide dismutase (EC 1.15.1.1), a superoxide reductase (EC 1.15.1.2), a xanthine dehydrogenase (EC 1.17.1.4), a xanthine oxidase (EC 1.17.3.2), a 6-hydroxynicotinate dehydrogenase (EC 1.17.3.3), a reticuline oxidase (EC 1.21.3.3), and a ribulose-bisphosphate carboxylase (EC 4.1.1.39).

4. The catalyst-enzyme composite film structure according to claim 1, wherein the catalyst particles for increasing the rate of the electrochemical reaction carry out an electrochemical oxidation-reduction reaction with hydrogen peroxide ($H_2O_2$).

5. The catalyst-enzyme composite film structure according to claim 4, wherein the catalyst particles for catalyzing the oxidation reduction of hydrogen peroxide comprise a unary metal (M), a binary metal (M-X), a unary metal oxide (MOy), a binary metal oxide (MOy-XOy), a metal-metal oxide composite material (M-MOy) or a combination of which, wherein y is smaller than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb.

6. The catalyst-enzyme composite film structure according to claim 5, wherein the catalyst particles comprise the binary metal and the binary metal oxide, and a molar ratio of the metal of the catalyst particles is larger than 0 and smaller than 100%.

7. The catalyst-enzyme composite film structure according to claim 1, wherein the catalyst particles are a plurality of nano PtIr catalyst particles, and the enzymes are a plurality of glucose oxidases (GOD).

8. The catalyst-enzyme composite film structure according to claim 1, wherein a support of the catalyst particles is a carbon black.

9. The catalyst-enzyme composite film structure according to claim 1, wherein an average diameter of the catalyst particles is between about 0.5 nm and about 100 μm.

* * * * *